US006632834B2

(12) United States Patent
Thompson et al.

(10) Patent No.: US 6,632,834 B2
(45) Date of Patent: Oct. 14, 2003

(54) COMPOSITIONS AND METHODS FOR TREATING CONDITIONS RESPONSIVE TO ESTROGEN

(75) Inventors: David D. Thompson, Gales Ferry, CT (US); Andrew G. Lee, Old Lyme, CT (US); Wesley W. Day, Old Lyme, CT (US); Robert L. Rosati, Stonington, CT (US)

(73) Assignee: Pfizer Inc., New York, NY (US)

( * ) Notice: Subject to any disclaimer, the term of this patent is extended or adjusted under 35 U.S.C. 154(b) by 50 days.

(21) Appl. No.: 09/758,778

(22) Filed: Jan. 11, 2001

(65) Prior Publication Data

US 2001/0041718 A1 Nov. 15, 2001

Related U.S. Application Data

(60) Provisional application No. 60/175,752, filed on Jan. 12, 2000.

(51) Int. Cl.$^7$ ............................................. A61K 31/40
(52) U.S. Cl. ...................................................... 514/428
(58) Field of Search ......................................... 514/428

(56) References Cited

U.S. PATENT DOCUMENTS

| 5,441,986 A | 8/1995 | Thompson |
| 5,552,412 A | 9/1996 | Cameron et al. |
| 5,827,892 A | 10/1998 | Löser et al. |
| 5,852,059 A | 12/1998 | Thompson |
| 5,902,830 A | 5/1999 | Löser et al. |
| 5,998,402 A | 12/1999 | Miller et al. |
| 6,107,331 A | 8/2000 | MacLean et al. |

FOREIGN PATENT DOCUMENTS

| EP | 0792641 | 3/1997 |
| EP | 0792646 | 3/1997 |
| EP | 0869132 | 7/1999 |
| WO | WO9908682 | 2/1999 |

OTHER PUBLICATIONS

Grodstein et al., American Journal of Medicine 1999;106:574–582.*
Paganini–Hill A, "Estrogen replacement therapy and colorectal cancer risk in elderly women" Dis. Colon Rectum 1999 42(10):1300–1305.*
Dunn, B.K. et al., *Hematology/Oncology Clinics of North America* (1998), Cancer Chemoprevention, vol. 12, No. 5, Oct. 1998, 1019–1036, Phase III, Large–Scale Chemoprevention Trials.

* cited by examiner

*Primary Examiner*—Sreeni Padmanabhan
*Assistant Examiner*—San-ming Hui
(74) *Attorney, Agent, or Firm*—Peter C. Richardson; Gregg C. Benson; Todd M. Crissey

(57) ABSTRACT

This invention relates to methods, pharmaceutical compositions and kits useful in treating conditions responsive to estrogen by the administration of estrogen agonists/antagonists. Conditions responsive to the compositions and methods include rheumatoid arthritis, colon cancer, tissue wounds, skin wrinkles and cataracts. The compositions are comprised of an estrogen agonist/antagonist and a pharmaceutically acceptable vehicle, carrier or diluent. The compositions and methods of treatment are effective while substantially reducing the concomitant liability of adverse effects associated with estrogen administration.

2 Claims, 1 Drawing Sheet

COMPOSITIONS AND METHODS FOR TREATING CONDITIONS RESPONSIVE TO ESTROGEN

CROSS REFERENCE TO RELATED APPLICATION

This application claims priority of U.S. provisional application No. 60/175,752, filed Jan. 12, 2000.

FIELD OF THE INVENTION

This invention relates to compositions and methods for treating conditions responsive to estrogen. The compositions and methods utilize estrogen agonist/antagonist compounds. In both men and post-menopausal women, conditions such as rheumatoid arthritis, colon cancer, tissue wounds, skin wrinkles and cataracts are treated with the compositions and methods of the present invention.

BACKGROUND OF THE INVENTION

In premenopausal women, 17β-estradiol produced by the ovaries is the chief circulating estrogen. Serum estradiol concentrations are low in preadolescent girls and increase at menarche. In women, they range from about 100 pg per milliliter (367 pmol per liter) in the follicular phase to about 600 pg per milliliter (2200 pmol per liter) at the time of ovulation. They may rise to nearly 20,000 pg per milliliter (70,000 pmol per liter) during pregnancy. After menopause, serum estradiol concentrations fall to values similar to or lower than those in men of similar age (5 to 20 pg per milliliter [18 to 74 pmol per liter]) (Yen, S. S. C. and Jaffe, R. B., eds. *Reproductive Endocrinology: Physiology, Pathophysiology and Clinical Management,* 3rd ed. Philadelphia: W. B. Saunders, (1991)).

Steroidal estrogens are formed ultimately from either androstenedione or testosterone as immediate precursors. The reaction involves aromatization of the A ring, and it is catalyzed in three steps by a monooxygenase enzyme complex (aromatase) that uses NADPH and molecular oxygen as cosubstrates, (Miller, W. L., *Endocr. Rev.,* 9:295–318 (1988)). In the first step of the reaction, C 19 (the angular methyl group residing on C 10 of the androgen precursor) is hydroxylated. A second hydroxylation results in the elimination of the newly formed C 19 hydroxymethyl group, and a final hydroxylation on C 2 results in the formation of an unstable intermediate that rearranges to form the phenolic A ring. The entire reaction consumes three molecules of NADPH.

Aromatase activity resides within a transmembrane glycoprotein ($P_{450,arom}$) that is homologous with the cytochrome $P_{450}$ family of monooxygenases (Nebert, D. W. and Gonzalez, F. J., *Annu. Rev. Biochem.* 56:945–993, (1987); Corbin, C. J., et al., *Proc. Natl. Acad. Sci. USA,* 85:8948–8952, (1988)); also essential is a ubiquitous flavoprotein, NADPH-cyctochrome $P_{450}$ reductase. Both proteins are localized in the endoplasmic reticulum of ovarian granulosa cells, testicular Sertoli and Leydig cells, adipocytes, placental synctiotrophoblasts, the preimplantation blastocyst, and various brain regions, including the hypothalamus.

The ovaries are the principle source of estrogen in premenopausal women. The major secretory product is estradiol, synthesized by granulosa cells from androgenic precursors provided by thecal cells. Secreted estradiol is oxidized reversibly to estrone, and both of these estrogens can be converted to estriol. These transformations take place mainly in the liver, where interconversion between estrone and estradiol is catalyzed by 17-hydroxysteroid dehydrogenase.

In men and postmenopausal women, the principle source of estrogen is adipose tissue. In this and in other peripheral tissues, estrone is synthesized from dehydroepiandrosterone, which is secreted by the adrenal cortex. Thus, the contribution of adipose tissue estrogens is regulated, in part by the availability of androgenic precursors (Mendelson, C. R. and Simpson, E. R., *Mol. Cell Endocrinol.,* 52:169–176, (1987)).

Autoimmune diseases, such as rheumatoid arthritis, involve aberrant regulation of cellular and humoral mediated immunity and are frequently associated with abnormal or enhanced T cell, B cell and macrophage effector functions directed towards self antigens. The activation of these cellular components towards self antigens is believed related to the break in feedback mechanisms associated with self tolerance. Autoimmune diseases encompass a whole spectrum of clinical entities and despite the differences in the target organ have many similarities. These include their preponderance in females of child bearing age with a female to male ratio varying from 50:1 in Hashimoto's thyroiditis to 10:1 in systemic lupus erythematosus (SLE) to 2:1 in Myasthenia gravis (Ahmed et al., *Am J. Path.,* 121:531 (1985)). In addition, these diseases are all characterized by the chronicity, the tendency of clinical remission and "flare ups" for poorly understood reasons, and the involvement of other organs. While the presence of autoantibodies, inappropriate expression of class II antigens, macrophage activation and T cell infiltration to the target organ have been described in essentially all of the autoimmune diseases, neither the triggering mechanisms which result in disease activation nort disease progression are well understood. Accordingly, therapy for these diseases is largely unsatisfactory and involves the use of gold salts, methotrexate, antimalarials, glucocorticoids (methylprednisolone), and other immunosuppressives as well as plasmaphoresis and attempts at inducing tolerance. Treatment of autoimmune diseases has not improved significantly over the past decade and primarily is associated with the use of nonsteroidal and steroidal anti-inflammatory agents to treat the symptoms of the disease. Clearly while suppression of the specific immune response directed against the host is necessary, generalized immunosuppression as with glucocorticoids has major liabilities in terms of side effect profile and the propensity of the immunosuppressed subject to be at greater risk for other infectious and non-infectious diseases.

Polymorphonuclear leukocytes (PMNL) play a regulatory role in inflammatory diseases. These cells, when activated, synthesize and release oxygen-centered molecules, chemoattractants, and hydrolytic enzymes. There is evidence that the oxygen-centered molecules play a detrimental role in a number of diseases such as chronic inflammatory diseases, rheumatoid arthritis, SLE, and others. In the case of an autoimmune disease, SLE, for example, the initiation of an inflammatory response is self antigen stimulating one's host neutrophils or PMNLs to secrete strong oxidants which damage surrounding cells and tissue.

Estrogen appears to be involved with autoimmune diseases although its role in disease progression or regression is complex and dependent on the nature of the autoimmune disease. Estrogen for example appears to have ameliorating effect on rheumatoid arthritis while having an exacerbating effect on systemic lupus (Chander & Spector; *Ann. Rheum. Dis.* 50:139). As reported by Jansson (*Free Rad. Res. Comms.,* 14(3):195–208, (1991)), estrogen increased the activity of an enzyme generated by PMNLS, myeloperoxidase, which regulates the production of oxidants from hydrogen peroxide. This enzyme converts hydrogen peroxide to hypochlorous acid, a strong oxidant. By increasing the enzyme's activity, and thus the presence of hypochlorous acid, the likelihood of increased oxidative stress on tissues, cells and various macromolecules in chronic inflammatory/autoimmune diseases is enhanced.

EP 664 125 A1 reports that inhibition of myeloperoxidase may be accomplished by treatment with certain 3-aroyl benzothiophines. Excess myeloperoxidase is associated with conditions which include systemic lupus erythematosis, Hashimoto's thyroiditis, myasthenia gravis, rheumatoid arthritis and multiple sclerosis.

Estrogen has been demonstrated to have a suppressive role on T cell function and yet an immunostimulatory effect on B cells. Therefore, estrogen-like compounds should prove beneficial in diseases associated with activated T cells including rheumatoid arthritis, multiple sclerosis, Guillan Barre syndrome and Hashimoto's thyroiditis through inhibition of T cell function (Holmadahl, J., *Autoimmun.* 2:651 (1989).

In addition to the suppressive effects of estrogen on T cells, estrogen may have additional protective roles. Marui et al., (*J. Clin. Invest.* 92:1866 (1993)) have recently reported that antioxidants suppress endothelial expression of VCAM-1. VCAM-1 is the ligand for VLA4, the T cell and macrophage integrin associated with trafficking of these cells out of the vasculature and into the perivascular space and target organs. As estrogen is an antioxidant, it would be anticipated that estrogen and related analogs will inhibit VLA-4 dependent trafficking of cells and thus hinder the immune cascade associated with autoimmune mediated disease.

Estrogen plays a detrimental role in other autoimmune diseases including systemic lupus and glomerulonephritis, diseases associated with immune complexes. While the mechanism(s) responsible for estrogen mediated disease progression are not known, the ability of estrogen to increase Fc mediated phagocytosis (Friedman et al., *J. Clin. Invest.* 76:162 (1985), and class 11 antigen expression and IL-1 production by macrophages from estrogen treated rodents (Flynn, *Life Sci.*, 38:2455 (1986) has been reported. Enhancement of these macrophage mediated effector functions would be expected to contribute towards the immune cascade associated with self destruction.

Cancer of the large bowel is second only to lung cancer as a cause of cancer death in the United States. Approximately 133,500 new cases occurred in 1996, resulting in 54,900 deaths. The incidence rate for this extremely common malignant condition has not changed substantially during the past 40 years, although, for some reason, the mortality rate has decreased in recent years, particularly in females. Colorectal cancer generally occurs in individuals 50 years of age or older.

Most colorectal cancers, regardless of etiology, are believed to arise from adenomatous polyps. A polyp is a grossly visible protrusion from the mucosal surface and may be classified pathologically as a nonneoplastic hamartoma (juvenile polyp), a hyperplastic mucosal proliferation (hyperplastic polyp), or an adenomatous polyp. Only adenomas are clearly premalignant, and only a minority of such lesions ever develop into cancer. Population-screening studies and autopsy surveys have revealed that adenomatous polyps may be found in the colons of about 30 percent of middle-aged or elderly people. Based on this prevalence and the known incidence of colorectal cancers, it appears that fewer than 1 percent of polyps ever become malignant. Most polyps produce no symptoms and remain clinically undetected. Occult blood in the stool may be found in fewer than 5 percent of subjects with such lesions.

A number of molecular changes have been described in DNA obtained from adenomatous polyps, dysplastic lesions, and polyps containing microscopic foci of tumor cells (carcinoma in situ), which are thought to represent a multistep process in the evolution of normal colonic mucosa to life-threatening invasive carcinoma. These developmental steps towards carcinogenesis include point mutations in the K-ras proto-oncogene; hypomethylation of DNA, leading to gene activation; loss of DNA ("allelic loss") at the site of a tumor suppressor gene [the adenomatous polyposis coli (APC) gene] located on the long arm of chromosome 5 (5q21); allelic loss at the site of a tumor suppressor gene located on chromosome 18q [so-called the deleted in colorectal cancer (DCC) gene]; and allelic loss at chromosome 17p, associated with mutations in the p53 tumor suppressor gene. Thus, the altered proliferative pattern of the colonic mucosa, which results in progression to a polyp and then to carcinoma, may involve the mutational activation of an oncogene followed by and coupled with a loss of genes that normally suppress tumorigenesis. While the present model includes five such molecular alterations, others are likely involved in the carcinogenic process. It remains uncertain whether the genetic aberrations always occur in a defined order. Based on this model, however, it is believed that neoplasia develops only in those polyps in which all of these mutational events take place. (Mayer, R. J., *Gastrointestinal Tract Cancer*, Chapter 92, in *Harrison's Principles of Internal Medicine*, 14th ed., 1998).

Several orally administered synthetic and naturally occurring materials have been assessed as possible inhibitors of colon cancer. The most effective class of these chemopreventive agents is aspirin and other nonsteroidal anti-inflammatory drugs, which are thought to suppress cell proliferation by inhibiting prostaglandin synthesis. Case-control studies have indicated that regular aspirin use reduces the risk for colonic adenomas and carcinomas as well as for death from large-bowel cancer; this inhibiting effect on colonic carcinogenesis appears to increase with the duration of drug use. While antioxidant vitamins such as ascorbic acid, tocopherols, and β-carotene are present in diets rich in fruits and vegetables, which have been associated with lower rates of colorectal cancer, they have been found to be ineffective in a prospectively randomized trial as a means of reducing the incidence of subsequent adenomas in subjects who had undergone the removal of a colonic adenoma. Estrogen replacement therapy has been associated in prospective cohort studies with a reduction in the risk of colorectal cancer in women, conceivably by an effect on bile acid synthesis and composition. The otherwise unexplained reduction in colorectal cancer mortality in women may be a result of the widespread use of estrogen replacement in postmenopausal individuals. (Mayer, R. J., *Gastrointestinal Tract Cancer*, Chapter 92, in *Harrison's Princilles of Internal Medicine*, 14th ed., 1998).

Wound healing is usually a coordinated, stereotyped sequence of events that includes (a) tissue disruption and loss of normal tissue architecture; (b) cell necrosis and hemorrhage; hemostasis (clot formation); (c) infiltration of segmented and mononuclear inflammatory cells, with vascular congestion and tissue edema; (d) dissolution of the clot as well as damaged cells and tissues by mononuclear cells (macrophages) (e) formation of granulation tissue (fibroplasia and angiogenesis). This sequence of cellular events has been observed in wounds from all tissues and organs generated in a large number of mammalian species (Gailet et al., 1994, *Curr. Opin. Cell. Biol.* 6:717–725).

Estrogen accelerates endothelial cell growth in vitro and in vivo (Morales, D. E., et al., *Circulation*, 91:755–63 (1995); Krasinski, K., et al., *Circulation*, 95:1768–72 (1997)). The rapid reendothelialization induced by estrogen after vascular injury may be due in part to increased local expression of vascular endothelial growth factor. Estrogen also inhibits apoptosis of cultured human endothelial cells in an estrogen receptor-dependent manner (Spyridopoulos, I., et al., *Circulation*, 95:1505–14 (1997)). Early restoration of endothelial integrity by estrogen may contribute to the attenuation of the response to injury by increasing the availability of nitric oxide, which can directly inhibit the proliferation of smooth-muscle cells (Cornwell, T. L., et al., *Am. J. Physiol.*, 267:C1405–C1413 (1994)). Estrogen directly inhibits the migration and proliferation of smooth-muscle cells in vitro (Kolodgic, F. D., et al., *Am. J. Pathol.* 148: 969–76 (1996); Bhalla, R. C., et al., *Am. J. Physiol.*, 272:H1996–H2003 (1997)).

Currently available wound healing therapies involve the administration of therapeutic proteins. Such therapeutic proteins may include regulatory factors involved in the normal healing process such as systemic hormones, cytokines, growth factors and other proteins that regulate proliferation and differentiation of cells. Growth factors, cytokines and hormones reported to have such wound healing capacity include, for example, the transforming growth factor-β superfamily (TGF-β) of proteins (Cox, D. A., *Cell Biology International*, 19:357–371 (1995)) acidic fibroblast growth factor (FGF) (Slavin, J., *Cell Biology International*, 19:431–444 (1995)), macrophage-colony stimulating factor (M-CSF) and calcium regulatory agents such as parathyroid hormone (PTH).

Epidemological evidence suggests that estrogens may protect against cataracts. Although women are at higher risk of developing cataracts than are men, this increased risk comes after menopause, when estrogen has waned Livingston, P. M., et al., *Dev. Opthalmol.* 26:1–6, (1994); Klein, B. E., et al., *Arch. Ohthalmol.* 116:219–225, (1998)). In one study of 544 women, early onset of menopause was associated with a 2.9-fold risk of developing cataracts (Shibata, T., et al., *Dev. Opthalmol.* 26:25–33, (1994)). Moreover, the results of three small epidemiological studies suggest that postmenopausal estrogen replacement therapy reduces the incidence of cataracts (Klein, B. E., et al., *Arch. Ohthalmol.* 112:85–91, (1994); Cumming, R. G. and Mitchell, P., *Am. J. Epidemiol.*, 145:242–249, (1997); Benitez del Castillo, J. M., et al., *Ophthalmology*, 104:970–973, (1997)). An in vivo rat model of age-related cataracts suggests that the protective effect of estrogen is a genomic one (Bigsby, R. M., *Proc. Natl. Acad. Sci. USA*, 96:9328–9332, (1999)).

Breast cancer is a hormone-dependent disease. Women without functioning ovaries who never receive estrogen replacement do not develop breast cancer. The female-to-male ratio for the disease is about 150 to 1. A host of findings indicate that hormones play a critical role as promoters of the disease. For most epithelial malignancies, a log—log plot of incidence versus age shows a straight-line increase with every year of life. A similar plot for breast cancer shows the same straight line increase, but with a decrease in slope beginning at the age of menopause. The three dates in a woman's life that have a major impact on breast cancer incidence are age of menarche, age at first full-term pregnancy, and age of menopause. Women who experience menarche at age 16 have only 50 to 60 percent of the lifetime breast cancer risk of women who experience menarche at age 12. Similarly, menopause occurring 10 years before the median age (52 years), whether natural or surgically induced, reduces lifetime breast cancer risk by about 35 percent. Compared with nulliparous women, women who have a first full-term pregnancy by age 18 have 30 to 40 percent the risk of breast cancer. Thus, length of menstrual life—particularly the fraction occurring before the first full-term pregnancy—is a substantial component of the total risk of breast cancer. This factor can account for 70 to 80 percent of the variation in breast cancer frequency in different countries.

International variation has provided some of the most important clues on hormonal carcinogenesis. A woman living to age 80 in North America has 1 chance in 9 of developing invasive breast cancer. Asian women have one-fifth to one-tenth the risk of breast cancer of women in North America or Western Europe. Asian women have substantially lower concentrations of estrogens and progesterone. These differences cannot be explained on a genetic basis, because Asian women living in a Western environment have a risk identical to that of their Western counterparts. These women also differ markedly in height and weight from Asian women in Asia; height and weight are critical regulators of age of menarche and have substantial effects on plasma concentrations of estrogens. (Lippman, M. E., Breast Cancer, Chapter 91, in *Harrison's Principles of Internal Medicine*, 14th ed., 1998).

Menopause occurs naturally at an average age of 50 to 51 years in the USA. As ovaries age, response to pituitary gonadotropins (follicle-stimulating hormone [FSH] and luteinizing hormone [LH]) decreases, initially resulting in shorter follicular phases (thus, shorter menstrual cycles), fewer ovulations, decreased progesterone production, and more irregularity in cycles. Eventually, the follicle fails to respond and does not produce estrogen. The transitional phase, during which a woman passes out of the reproductive stage, begins before menopause. It is termed the climacteric or perimenopause, although many persons refer to it as menopause.

Premature menopause refers to ovarian failure of unknown cause that occurs before age 40. It may be associated with smoking, living at high altitude, or poor nutritional status. Artificial menopause may result from oophorectomy, chemotherapy, radiation of the pelvis, or any process that impairs ovarian blood supply.

Symptoms of the climacteric range from nonexistent to severe. Hot flushes (flashes) and sweating secondary to vasomotor instability affect 75% of women. Most have hot flushes for more than 1 year, and 25 to 50% for more than 5 years. The woman feels warm or hot and may perspire, sometimes profusely. The skin, especially of the head and neck, becomes red and warm. The flush, which may last from 30 sec to 5 min, may be followed by chills. Vasomotor symptoms of the hot flush coincide with the onset of LH pulses, but not every increase in LH is associated with a hot flush, suggesting that hypothalamic control of LH pulses is independent of that of flushes. This independence is confirmed by the occurrence of hot flushes in women who have had pituitary failure and do not secrete LH and/or FSH.

Psychologic and emotional symptoms—including fatigue, irritability, insomnia, inability to concentrate, depression, memory loss, headache, anxiety, and nervousness and timidity can occur. Sleep disruption by recurrent hot flushes contributes to fatigue and irritability. Intermittent dizziness, paresthesias, palpitations, and tachycardia may also occur. Nausea, constipation, diarrhea, arthralgia, myalgia, cold hands and feet, and weight gain are also common.

The large reduction in estrogen leads to profound changes in the lower genital tract; e.g., the vaginal mucosa and vulvar skin become thinner, the normal bacterial flora changes, and the labia minora, clitoris, uterus, and ovaries decrease in size. Inflammation of the vaginal mucosa (atrophic vaginitis) can cause the mucosa to have a strawberry appearance and can lead to urinary frequency and urgency, vaginal dryness, and dyspareunia. Women tend to lose pelvic muscle tone and to develop urinary incontinence, cystitis, and vaginitis.

SUMMARY OF THE INVENTION

Figure 1:
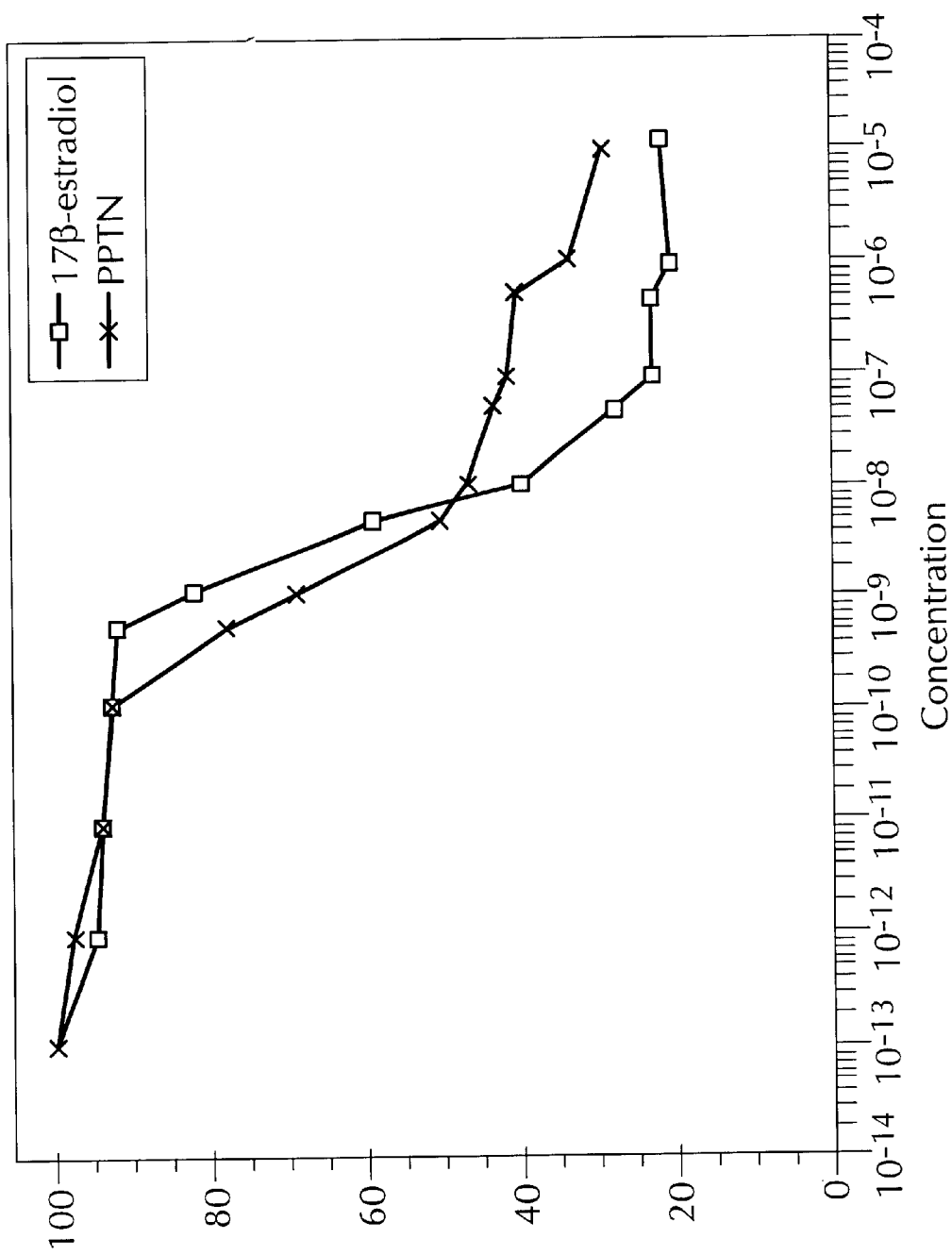
FIG. 1 is a log-linear competition binding plot of PPTN and 17β-estradiol to human estrogen receptor. The X-axis represents percentage of radiolabeled estrogen bound to receptor. The Y-axis represents the molar concentration of added ligand. Values are mean ±SEM.

This invention relates to pharmaceutical compositions useful for the treatment of conditions responsive to estrogen. The compositions are comprised of an estrogen agonist/antagonist and a pharmaceutically acceptable carrier, vehicle or diluent. These compositions are effective in treating rheumatoid arthritis, colon cancer, tissue wounds, skin wrinkles and cataracts.

A second aspect of the invention relates to methods of treating conditions responsive to estrogen. Specifically the methods relate to methods of treating rheumatoid arthritis, colon cancer, tissue wounds, skin wrinkles and cataracts. The methods comprise the administration of an effective amount of the estrogen agonists/antagonists as described herein.

A third aspect of the invention is that the compositions and methods of treating conditions responsive to estrogen such as rheumatoid arthritis, colon cancer, tissue wounds, skin wrinkles and cataracts are effective while substantially reducing the concomitant liability of adverse effects associated with estrogen administration.

As a fourth aspect, the present invention provides for kits for use by a consumer to treat conditions responsive to estrogen such as rheumatoid arthritis, colon cancer, tissue wounds, skin wrinkles and cataracts. The kit comprises a) a pharmaceutical composition comprising an estrogen agonist/antagonist of the present invention and a pharmaceutically acceptable carrier, vehicle or diluent; and b) instructions describing a method of using the pharmaceutical composition to treat conditions responsive to estrogen such as rheumatoid arthritis, colon cancer, tissue wounds, skin wrinkles and cataracts. The instructions may also indicate that the kit is for treatment of conditions responsive to estrogen such as rheumatoid arthritis, colon cancer, tissue wounds, skin wrinkles and cataracts while substantially reducing the concomitant liability of adverse effects associated with estrogen administration.

As a fifth aspect, the present invention provides for the use of estrogen agonists/antagonists of the present invention for the manufacture of a medicament to treat conditions responsive to estrogen such as rheumatoid arthritis, colon cancer, tissue wounds, skin wrinkles and cataracts. These indications are also treated by the medicament while substantially reducing the concomitant liability of adverse effects associated with estrogen administration.

A sixth aspect of the invention relates to topical formulations for the treatment of skin wrinkles. The topical pharmaceutical and cosmetic compositions of the present invention maybe made into a wide variety of product types. These include, but are not limited to lotions, creams, beach oils, gels, sticks, sprays, ointments, pastes, mousses and cosmetics. These product types may comprise several types of carrier systems including, but not limited to solutions, emulsions, gels and solids. The topical formulations comprise an effective amount of an estrogen agonist/antagonist and may optionally include other anti-wrinkle agents such as sunscreens and sunblocks, anti-inflammatory agents, antioxidants/radical scavengers, chelators, retinoids and N-acetyl-L-cysteine.

DETAILED DESCRIPTION OF THE INVENTION

The present invention relates to compositions and methods for treating conditions responsive to estrogen. Unless otherwise specified, the following terms have the meanings as defined below:

"Treatment" as used herein includes preventative (e.g., prophylactic) and palliative treatment and "treating" as used herein refers to the act of providing preventative and/or palliative treatment.

A "subject" is an animal including the human species that is treatable with the compositions, methods and kits of the present invention. The term "subject" or "subjects" is intended to refer to both the male and female gender unless one gender is specifically indicated.

"Conditions responsive to estrogen" include those conditions caused by estrogen deficiency or those which are treated with estrogen supplementation or replacement. These conditions include rheumatoid arthritis, colon cancer, tissue wounds, skin wrinkles and cataracts.

"Adverse effects associated with estrogen" include breast tenderness, breast cancer, bloating, headache, increased blood clotting and menstrual bleeding in women. Unopposed estrogen therapy increases the risk of endometrial carcinoma. Women on long-term estrogen therapy may have an increased risk that is not reversed by concurrent progestin (*N. Engl. J. Med.* 332:1589, (1995)). In men, the adverse effects of estrogen include increased blood clotting, gynecomastia, feminization and decreased libido.

The term "post-menopausal women" is defined to include not only women of advanced age who have passed through menopause, but also women who have been hysterectomized or for some other reason have suppressed estrogen production, such as those who have undergone long-term administration of corticosteroids, suffer from Cushions' syndrome or have gonadal dysgenesis.

"Breast cancer" is defined as a malignant proliferation of epithelial cells lining the ducts or lobules of the breast.

An "estrogen agonist/antagonist" is compound that affects some of the same receptors that estrogen does, but not necessarily all, and in some instances, it antagonises or blocks estrogen. It is also known as a "selective estrogen receptor modulator" (SERM). Estrogen agonists/antagonists may also be referred to as antiestrogens although they have some estrogenic activity at some estrogen receptors. Estrogen agonists/antagonists are therefore not what are commonly referred to as "pure antiestrogens". Antiestrogens that can also act as agonists are referred to as Type I antiestrogens. Type I antiestrogens activate the estrogen receptor to bind tightly in the nucleus for a prolonged time but with impaired receptor replenishment (Clark, et al., *Steroids* 22:707, 1(973); Capony, et al., *Mol Cell Endocrinol*, 3:233, (1975)).

The methods referred to above for treating conditions responsive to estrogen generally refer to benefits and/or survival in the long term. Clinical benefits may be observable within a few weeks, for example 2–3 weeks, however, this does not imply that the subjects are not benefiting from the treatment prior to actual clinical observation. It is preferred, however that administration be effected long term; that is for longer than 16 weeks, and preferably longer than 6 months.

Not being bound by any single theory, it is believed that the estrogen agonists/antagonists of the present invention and the compositions containing those estrogen agonists/antagonists treat conditions responsive to estrogen such as rheumatoid arthritis, colon cancer, tissue wounds, skin wrinkles and cataracts due to activity at the estrogen receptor. The estrogen agonists/antagonists of the present invention exert a positive estrogenic effect in animals in the treatment of rheumatoid arthritis, colon cancer, tissue wounds, skin wrinkles and cataracts. The effects are achieved without the concomitant liability of adverse effects associated with estrogen administration due to the estrogen agonists/antagonists antiestrogen effects in other tissues such as breast tissue.

The estrogen agonists/antagonists of the present invention include the compounds described in U.S. Pat. No. 5,552,412 which is incorporated in its entirety. The compounds are described by formula (I) given below:

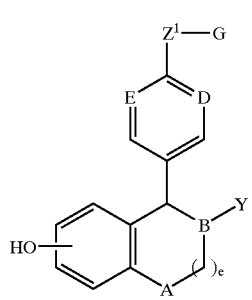

(I)

wherein:
A is selected from $CH_2$ and NR;
B, D and E are independently selected from CH and N;
Y is
  (a) phenyl, optionally substituted with 1–3 substituents independently selected from $R^4$;
  (b) naphthyl, optionally substituted with 1–3 substituents independently selected from $R^4$;
  (c) $C_3$–$C_8$ cycloalkyl, optionally substituted with 1–2 substituents independently selected from $R^4$;
  (d) $C_3$–$C_8$ cycloalkenyl, optionally substituted with 1–2 substituents independently selected from $R^4$;
  (e) a five membered heterocycle containing up to two heteroatoms selected from the group consisting of —O—, —$NR^2$— and —$S(O)_n$—, optionally substituted with 1–3 substituents independently selected from $R^4$;
  (f) a six membered heterocycle containing up to two heteroatoms selected from the group consisting of —O—, —$NR^2$— and —$S(O)_n$— optionally substituted with 1–3 substituents independently selected from $R^4$; or
  (g) a bicyclic ring system consisting of a five or six membered heterocyclic ring fused to a phenyl ring, said heterocyclic ring containing up to two heteroatoms selected from the group consisting of —O—, —$NR^2$— and —$S(O)_n$—, optionally substituted with 1–3 substituents independently selected from $R^4$;

$Z^1$ is
  (a) —$(CH_2)_p$ W$(CH_2)_q$—;
  (b) —$O(CH_2)_p$ $CR^5R^6$—;
  (c) —$O(CH_2)_p$W$(CH_2)_q$—;
  (d) —$OCHR^2CHR^3$—; or
  (e) —$SCHR^2CHR^3$—;

G is
  (a) —$NR^7R^8$;
  (b)

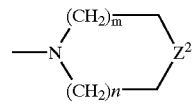

wherein n is 0, 1 or 2; m is 1, 2 or 3; $Z^2$ is —NH—, —O—, —S—, or —$CH_2$—; optionally fused on adjacent carbon atoms with one or two phenyl rings and, optionally independently substituted on carbon with one to three substituents and, optionally, independently on nitrogen with a chemically suitable substituent selected from $R^4$; or
  (c) a bicyclic amine containing five to twelve carbon atoms, either bridged or fused and optionally substituted with 1–3 substituents independently selected from $R^4$; or

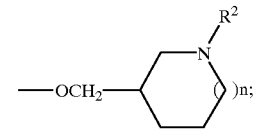

$Z^1$ and G in combination may be
W is
  (a) —$CH_2$—;
  (b) —CH=CH—;
  (c) —O—;
  (d) —$NR^2$—;
  (e) —$S(O)_n$—;
  (f)

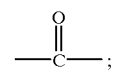

(g) —$CR^2(OH)$—;
  (h) —$CONR^2$—;
  (i) —$NR^2CO$—;
  (j)

or
  (k) —C≡C—;

R is hydrogen or $C_1$–$C_6$ alkyl;
$R^2$ and $R^3$ are independently
  (a) hydrogen; or
  (b) $C_1$–$C_4$ alkyl;

$R^4$ is
  (a) hydrogen;
  (b) halogen;
  (c) $C_1$–$C_6$ alkyl;
  (d) $C_1$–$C_4$ alkoxy;
  (e) $C_1$–$C_4$ acyloxy;
  (f) $C_1$–$C_4$ alkylthio;
  (g) $C_1$–$C_4$ alkylsulfinyl;
  (h) $C_1$–$C_4$ alkylsulfonyl;
  (i) hydroxy ($C_1$–$C_4$)alkyl;
  (j) aryl ($C_1$–$C_4$)alkyl;
  (k) —$CO_2H$;
  (l) —CN;
  (m) —CONHOR;
  (n) —$SO_2$NHR;
  (o) —$NH_2$;
  (p) $C_1$–$C_4$ alkylamino;
  (q) $C_1$–$C_4$ dialkylamino;
  (r) —$NHSO_2R$;
  (s) —$NO_2$;
  (t) -aryl; or
  (u) —OH;

$R^5$ and $R^6$ are independently $C_1$–$C_8$ alkyl or together form a $C_3$–$C_{10}$ carbocyclic ring;

$R^7$ and $R^8$ are independently
  (a) phenyl;
  (b) a $C_3$–$C_{10}$ carbocyclic ring, saturated or unsaturated;
  (c) a $C_3$–$C_{10}$ heterocyclic ring containing up to two heteroatoms, selected from —O—, —N— and —S—;
  (d) H;
  (e) $C_1$–$C_6$ alkyl; or
  (f) form a 3 to 8 membered nitrogen containing ring with $R^5$ or $R^6$;

$R^7$ and $R^8$ in either linear or ring form may optionally be substituted with up to three substituents independently selected from $C_1$–$C_6$ alkyl, halogen, alkoxy, hydroxy and carboxy;

a ring formed by $R^7$ and $R^8$ may be optionally fused to a phenyl ring;

e is 0, 1 or 2;
m is 1, 2 or 3;
n is 0, 1 or 2;
p is 0, 1, 2 or 3;
q is 0, 1, 2 or 3;

and optical and geometric isomers thereof; and nontoxic pharmacologically acceptable acid addition salts, N-oxides, esters, quaternary ammonium salts and prodrugs thereof.

By halo is meant chloro, bromo, iodo, or fluoro or by halogen is meant chlorine, bromine, iodine or fluorine.

By alkyl is meant straight chain or branched saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, hexyl and isohexyl.

By alkoxy is meant straight chain or branched saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, hexoxy and isohexoxy.

The parenthetical negative or positive sign used herein in the nomenclature denotes the direction plane polarized light is rotated by the particular stereoisomer.

Additional preferred compounds of the invention, which are also disclosed in U.S. Pat. No. 5,552,412 are of the formula (IA):

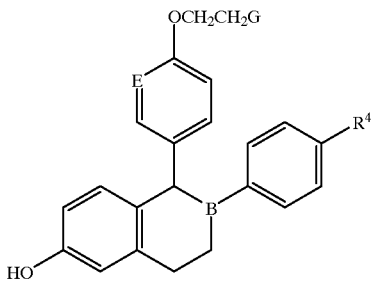

(IA)

wherein G is

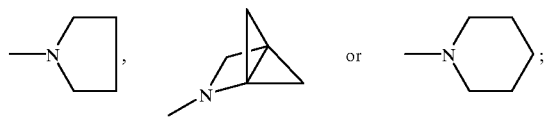

$R^4$ is H, OH, F, or Cl; and B and E are independently selected from CH and N.

Especially preferred compounds of the invention for the compositions and methods are:

cis-6-(4-fluoro-phenyl)-5-[4-(2-piperidin-1-yl-ethoxy)-phenyl]-5,6,7,8-tetrahydro-naphthalene-2-ol;

(−)-cis-6-phenyl-5-[4-(2-pyrrolidin-1-yl-ethoxy)-phenyl]-5,6,7,8-tetrahydro-naphthalene-2-ol;

cis-6-phenyl-5-[4-(2-pyrrolidin-1-yl-ethoxy)-phenyl]-5,6,7,8-tetrahydro-naphthalene-2-ol;

cis-1-[6'-pyrrolidinoethoxy-3'-pyridyl]-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-[4-(2-piperidin-1-yl-ethoxy)-phenyl]-5,6,7,8-tetrahydro-naphthalene-2-ol;

1-(4'-pyrrolidinolethoxyphenyl)-2-phenyl-6-hydroxy-1,2,3,4-tetrahydroisoquinoline and their salts. An especially preferred salt of (−)-cis-6-phenyl-5-[4-(2-pyrrolidin-1-yl-ethoxy)-phenyl]-5,6,7,8-tetrahydro-naphthalene-2-ol is the tartrate salt.

Other preferred estrogen agonists/antagonists are described in U.S. Pat. No. 5,047,431. The structure of these compounds is given by formula (II) below:

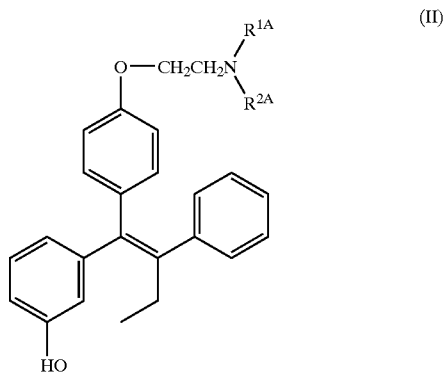

(II)

wherein
  $R^{1A}$ and $R^{2A}$ may be the same or different provided that, when $R^{1A}$ and $R^{2A}$ are the same, each is a methyl or ethyl group, and, when $R^{1A}$ and $R^{2A}$ are different, one of them is a methyl or ethyl group and the other is hydrogen or a benzyl group; and pharmaceutically acceptable salts and prodrugs thereof.

Additional preferred estrogen agonists/antagonists are tamoxifen: (ethanamine, 2-[-4-(1,2-diphenyl-1-butenyl) phenoxy]-N,N-dimethyl, (Z)-2-, 2-hydroxy-1,2,3-propanetricarboxylate(1:1)) and other compounds as disclosed in U.S. Pat. No. 4,536,516; 4-hydroxy tamoxifen (i.e., tamoxifen wherein the 2-phenyl moiety has a hydroxy group at the 4 position) and other compounds as disclosed in U.S. Pat. No. 4,623,660; raloxifene: (methanone, [6-hydroxy-2-(4-hydroxyphenyl)benzo[b]thien-3-yl][4-[2-(1-piperidinyl)ethoxy]phenyl]-,hydrochloride) and other compounds as disclosed in U.S. Pat. Nos. 4,418,068, 5,393,763, 5,457,117, 5,478,847 and 5,641,790; toremifene: (ethanamine, 2-[4-(4-chloro-1,2-diphenyl-1-butenyl) phenoxy]-N,N-dimethyl-, (Z)-, 2-hydroxy-1,2,3-propanetricarboxylate (1:1) and other compounds as disclosed in U.S. Pat. Nos. 4,696,949 and 4,996,225; centchroman: 1-[2-[[4-(-methoxy-2,2, dimethyl-3-phenyl-chroman-4-yl)-phenoxy]-ethyl]-pyrrolidine and other compounds as disclosed in U.S. Pat. No. 3,822,287; idoxifene: pyrrolidine, 1-[-[4-[[1-(4-iodophenyl)-2-phenyl-1-butenyl] phenoxy]ethyl] and other compounds as disclosed in U.S. Pat. No. 4,839,155; 6-(4-hydroxy-phenyl)-5-[4-(2-piperidin-1-yl-ethoxy)-benzyl]-naphthalen-2-ol and other compounds as disclosed in U.S. Pat. No. 5,484,795; and {4-[2-(2-aza-bicyclo[2.2.1]hept-2-yl)-ethoxy]-phenyl}-[6-hydroxy-2-(4-hydroxy-phenyl)-benzo[b]thiophen-3-yl]-methanone and other compounds as disclosed in published international application WO 95/10513. Other preferred compounds include GW 5638 and GW 7604. The synthesis of these compounds is described in Willson et al., *J. Med. Chem.*, 1994;37:1550–1552.

Further preferred estrogen agonists/antagonists include EM-652 (as shown in the formula designated herein as formula (III)) and EM-800 (as shown in the formula designated herein as formula (IV)). The synthesis of EM-652 and EM-800 and the activity of various enantiomers is described in Gauthier et al., *J. Med. Chem.*, 1997;40:2117–2122.

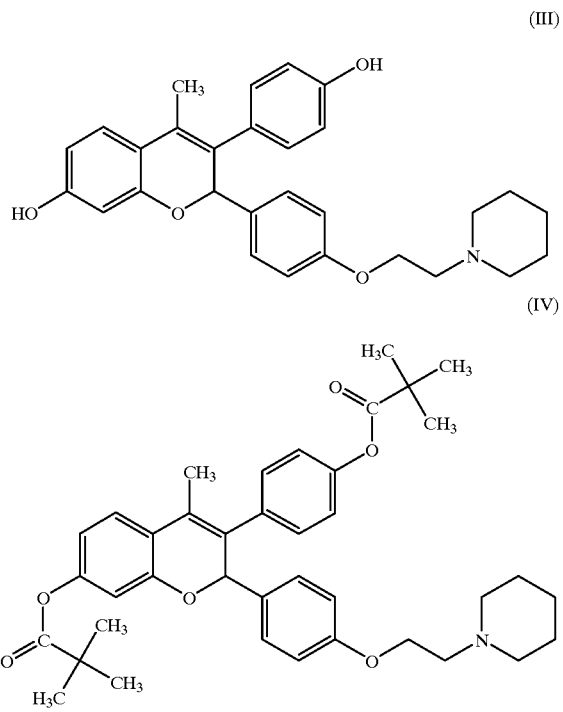

Further preferred estrogen agonists/antagonists include TSE 424 and other compounds disclosed in U.S. Pat. No. 5,998,402, U.S. Pat. No. 5,985,910, U.S. Pat. No. 5,780,497, U.S. Pat. No. 5,880,137, and European Patent Application EP 0802183 A1 including the compounds described by the formulae designated herein as formulae V and VI, below:

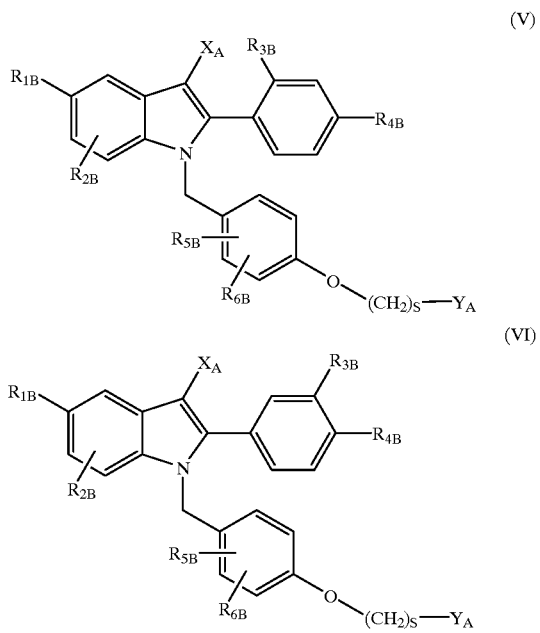

wherein:

$R_{1B}$ is selected from H, OH or the $C_1$–$C_{12}$ esters (straight chain or branched) or $C_1$–$C_{12}$ (straight chain or branched or cyclic) alkyl ethers thereof, or halogens; or $C_1$–$C_4$ halogenated ethers including trifluoromethyl ether and trichloromethyl ether.

$R_{2B}$, $R_{3B}$, $R_{4B}$, $R_{5B}$, and $R_{6B}$ are independently selected from H, OH or the $C_1$–$C_{12}$ esters (straight chain or branched) or $C_1$–$C_{12}$ alkyl ethers (straight chain or branched or cyclic) thereof, halogens, or $C_1$–$C_4$ halogenated ethers including trifluoromethyl ether and trichloromethyl ether, cyano, $C_1$–$C_6$ alkyl (straight chain or branched), or trifluoromethyl;

$X_A$ is selected from H, $C_1$–$C_6$ alkyl, cyano, nitro, trifluoromethyl, and halogen;

s is 2 or 3;

$Y_A$ is selected from:

a) the moiety:

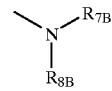

wherein $R_{7B}$ and $R_{8B}$ are independently selected from the group of H, $C_1$–$C_6$ alkyl, or phenyl optionally substituted by CN, $C_1$–$C_6$ alkyl (straight chain or branched), $C_1$–$C_6$ alkoxy (straight chain or branched), halogen, —OH, —$CF_3$, or —$OCF_3$;

b) a five-membered saturated, unsaturated or partially unsaturated heterocycle containing up to two heteroatoms selected from the group consisting of —O—, —NH—, —N($C_1$–$C_4$ alkyl)-, —N=, and —S(O)$_u$—, wherein u is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$-$C_4$)alkyl, —$CO_2H$, —CN, —CONHR$_{1B}$, —NH$_2$, $C_1$-$C_4$ alkylamino, di($C_1$-$C_4$)alkylamino, —NHSO$_2$R$_{1B}$, —NHCOR$_{1B}$, —NO$_2$, and phenyl optionally substituted with 1–3 ($C_1$-$C_4$)alkyl;

c) a six-membered saturated, unsaturated or partially unsaturated heterocycle containing up to two heteroatoms selected from the group consisting of —O—, —NH—, —N($C_1$-$C_4$ alkyl)-, —N=, and —S(O)$_u$—, wherein u is an integer of from 0–2, optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, Cl-$C_4$ alkylsulfinyl, $C_1$-$C_4$ alkylsulfonyl, hydroxy ($C_1$-$C_4$)alkyl, —$CO_2H$, —CN, —CONHR$_1$, —NH$_2$, $C_1$-$C_4$ alkylamino, di($C_1$-$C_4$)alkylamino, —NHSO$_2$R$_{1B}$, —NHCOR$_{1B}$, —NO$_2$, and phenyl optionally substituted with 1–3 ($C_1$-$C_4$)alkyl;

d) a seven-membered saturated, unsaturated or partially unsaturated heterocycle containing up to two heteroatoms selected from the group consisting of —O—, —NH—, —N($C_1$-$C_4$ alkyl)-, —N=, and —S(O)$_u$—, wherein u is an integer of from 0–2, optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C4$ alkylsulfonyl, hydroxy ($C_1$-$C_4$)alkyl, —$CO_2H$, —CN, —CONHR$_{1B}$, —NH$_2$, $C^1$-$C_4$ alkylamino, di($C_1$-$C_4$)alkylamino, —NHSO$_2$R$_{1B}$, —NHCOR$_{1B}$, —NO$_2$, and phenyl optionally substituted with 1–3 ($C_1$-$C_4$)alkyl; or e) a bicyclic heterocycle containing from 6–12 carbon atoms either bridged or fused and containing up to two heteroatoms selected from the group consisting of —O—, —NH—, —N($C_1$-$C_4$ alkyl)—, and —S(O)$_u$—, wherein u is an integer of from 0–2, optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy ($C_1$-$C_4$)alkyl, —$CO_2H$—, —CN—, —CONHR$_{1B}$—, —NH$_2$, —N=, $C_1$-$C_4$ alkylamino, di($C_1$-$C_4$) alkylamino, —NHSO$_2$R$_{1B}$, —NHCOR$_{1B}$, —NO$_2$, and phenyl optionally substituted with 1–3 ($C_1$-$C_4$) alkyl; and optical and geometric isomers thereof; and nontoxic pharmacologically acceptable acid addition salts, N-oxides, esters, quaternary ammonium salts, and prodrugs thereof.

The more preferred compounds of this invention are those having the general structures V or VI, above, wherein:

R$_{1B}$ is selected from H, OH or the $C_1$-$C_{12}$ esters or alkyl ethers thereof, and halogen;

R$_{2B}$, R$_{3B}$, R$_{4B}$, R$_{5B}$, and R$_{6B}$ are independently selected from H, OH or the $C_1$-$C_{12}$ esters or alkyl ethers thereof, halogen, cyano, $C_1$-$C_6$ alkyl, or trihalomethyl, preferably trifluoromethyl, with the proviso that, when R$_{1B}$ is H, R$_{2B}$ is not OH;

X$_A$ is selected from H, $C_1$-$C_6$ alkyl, cyano, nitro, trifluoromethyl, and halogen;

Y$_A$ is the moiety:

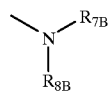

R$_{7B}$ and R$_{8B}$ are selected independently from H, $C_1$-$C_6$ alkyl, or combined by —(CH$_2$)$_w$—, wherein w is an integer of from 2 to 6, so as to form a ring, the ring being optionally substituted by up to three substituents selected from the group of hydrogen, hydroxyl, halo, $C_1$-$C_4$ alkyl, trihalomethyl, $C_1$-$C_4$ alkoxy, trihalomethoxy, $C_1$-$C_4$ alkylthio, $C_1$-$C_4$ alkylsulfinyl, $C_1$-$C_4$ alkylsulfonyl, hydroxy ($C^1$-$C_4$)alkyl, —$CO_2H$, —CN, —CONH($C_1$-$C_4$alkyl), —NH$_2$, $C_1$-$C_4$ alkylamino, $C_1$-$C_4$ dialkylamino, —NHSO$_2$ ($C_1$-$C_4$alkyl), —CO($C_1$-$C_4$alkyl), and —NO$_2$; and optical and geometric isomers thereof; and nontoxic pharmacologically acceptable acid addition salts, N-oxides, esters, quaternary ammonium salts, and prodrugs thereof.

The rings formed by a concatenated R$_{7B}$ and R$_{8B}$, mentioned above, may include, but are not limited to, aziridine, azetidine, pyrrolidine, piperidine, hexamethyleneamine or heptamethyleneamine rings.

The most preferred compounds of structural formulas V and VI, above, are those wherein R$_{1B}$ is OH; R$_{2B}$–R$_{6B}$ are as defined above; X$_A$ is selected from the group of Cl, NO$_2$, CN, CF$_3$, or CH$_3$; Y$_A$ is the moiety

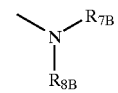

and R$_{7B}$ and R$_{8B}$ are concatenated together as —(CH$_2$)$_t$—, wherein t is an integer of from 4 to 6, to form a ring optionally substituted by up to three subsituents selected from the group of hydrogen, hydroxyl, halo, $C_1$-$C_4$ alkyl, trihalomethyl, $C_1$-$C_4$ alkoxy, trihalomethoxy, $C_1$-$C_4$ alkylthio, $C_1$-$C_4$ alkylsulfinyl, $C_1$-$C_4$ alkylsulfonyl, hydroxy ($C_1$-$C_4$)alkyl, —$CO_2H$, —CN, —CONH($C_1$-$C_4$) alkyl, —NH$_2$$C_1$-$C_4$ alkylamino, di($C_1$-$C_4$)alkylamino, —NHSO$_2$($C_1$-$C_4$)alkyl, —NHCO($C_1$-$C_4$)alkyl, and —NO$_2$; and optical and geometric isomers thereof; and nontoxic pharmacologically acceptable acid addition salts, N-oxides, esters, quaternary ammonium salts, and prodrugs thereof.

Another preferred compound is TSE-424 as described by the formula designated herein as formula (Va) below:

(Va)

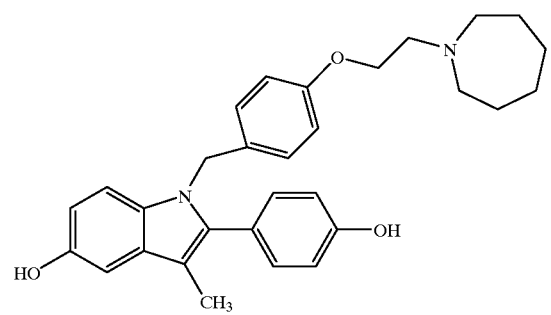

The chemist of ordinary skill will recognize that certain compounds of this invention will contain one or more atoms which may be in a particular stereochemical, tautomeric, or geometric configuration, giving rise to stereoisomers, tautomers and configurational isomers. All such isomers and mixtures thereof are included in this invention. Hydrates of the compounds of this invention are also included.

It is also part of the present invention to administer more than one estrogen agonist/antagonist. In addition, an estrogen agonist/antagonist or combinations of estrogen agonists/ antagonists can be administered in combination with other therapeutically active compounds, particularly compounds that are used to treat rheumatoid arthritis, colon cancer, tissue wounds or cataracts. The different compounds can be administered in the same dosage form or in different dosage forms at the same time or at different times.

The subject invention also includes isotopically-labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2$H, $^3$H, $^{13}$C$^{14}$C, $^{15}$N, $^{18}$F and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of Formula I of this invention and prodrugs thereof can generally be prepared by carrying out the procedures outlined and/or exemplified in U.S. Pat. No. 5,552,412 and by substituting a readily available isotopically labeled reagent for a non-isotopically labeled reagent.

Pharmaceutical chemists will easily recognize that physiologically active compounds which have accessible hydroxy groups are frequently administered in the form of pharmaceutically acceptable esters. The literature concerning such compounds, such as estradiol, provides a great number of instances of such esters. The compounds of this invention are no exception in this respect, and can be effectively administered as an ester, formed on the hydroxy groups, just as one skilled in pharmaceutical chemistry would expect. It is believed that such esters are metabolically cleaved in the body, yielding the compound with a free hydroxy group. It is possible, as has long been known in pharmaceutical chemistry, to adjust the rate or duration of action of the compound by appropriate choices of ester groups.

Certain ester groups are preferred as constituents of the compounds of this invention. The compounds of formula I or IA may contain ester groups at various positions as defined herein above, where these groups are represented as —COOR$_9$, R$_9$ is C$_1$–C$_4$ alkyl, C$_1$–C$_3$ chloroalkyl, C$_1$–C$_3$ fluoroalkyl, C$_5$–C$_7$ cycloalkyl, phenyl, or phenyl mono- or disubstituted with C$_1$–C$_4$ alkyl, C$_1$–C$_4$ alkoxy, hydroxy, nitro, chloro, fluoro or tri(chloro or fluoro)methyl.

The pharmaceutically acceptable acid addition salts of the compounds of this invention may be formed of the compound itself, or of any of its esters, and include the pharmaceutically acceptable salts which are often used in pharmaceutical chemistry. For example, salts may be formed with inorganic or organic acids such as hydrochloric acid, hydrobromic acid, hydroiodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferable with hydrochloric acid, citric acid, benzoic acid, maleic acid, acetic acid and propionic acid.

The compounds of this invention, as discussed above, can be administered in the form of acid addition salts. The salts are conveniently formed, as is usual in organic chemistry, by reacting a compound of this invention with a suitable acid, such as have been described above. The salts are quickly formed in high yields at moderate temperatures, and often are prepared by merely isolating the compound from a suitable acidic wash as the final step of the synthesis. The salt-forming acid is dissolved in an appropriate organic solvent, or aqueous organic solvent, such as an alkanol, ketone or ester. On the other hand, if a compound of this invention is desired in the free base form, it is isolated from a basic final wash step, according to the usual practice. A preferred technique for preparing hydrochlorides is to dissolve the free base in a suitable solvent and dry the solution thoroughly, as over molecular sieves, before bubbling hydrogen chloride gas through it. A preferred salt of the present invention is the D-(−)-tartrate salt.

The dose of a compound of this invention to be administered to a human is rather widely variable and subject to the judgement of the attending physician. It should be noted that it may be necessary to adjust the dose of a compound when it is administered in the form of a salt, such as a laurate, the salt forming moiety of which has an appreciable molecular weight. The general range of effective administration rates of the compounds is from about 0.001 mg/day to about 100 mg/day. A preferred rate range is from about 0.01 mg/day to 10 mg/day. Of course, it is often practical to administer the daily dose of compound in portions, at various hours of the day. However, in any given case, the amount of compound administered will depend on such factors as the solubility of the active component, the formulation used and the route of administration.

The route of administration of the compounds of this invention is not critical. The compounds are known to be absorbed from the alimentary tract, and so it is usually preferred to administer a compound orally for reasons of convenience. However, the compounds may equally effectively be administered percutaneously, or as suppositories for absorption by the rectum, if desired in a given instance. All of the usual types of compositions may be used, including tablets, chewable tablets, capsules, solutions, parenteral solutions, troches, suppositories and suspensions. Compositions are formulated to contain a daily dose, or a convenient fraction of daily dose, in a dosage unit, which may be a single tablet or capsule or convenient volume of a liquid.

In general, all of the compositions are prepared according to methods usual in pharmaceutical chemistry and by those procedures outlined and/or exemplified in U.S. Pat. No. 5,552,412.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant may be necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which facilitate the disintegration of a tablet to release a compound when the tablet becomes wet. They include starches, clays, celluloses, algins and gums, more particularly, corn and potato starches, methylcellulose, agar, bentonite, wood cellulose, powdered natural sponge, cation-exchange resins, alginic acid, guar gum, citrus pulp and carboxymethylcellulose, for example, may be used as well as sodium lauryl sulfate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

When it is desired to administer a compound as a suppository, the typical bases may be used. Cocoa butter is a traditional suppository base, which may be modified by addition of waxes to raise its melting point slightly. Water-miscible suppository bases comprising, particularly, polyethylene glycols of various molecular weights are in wide use.

The effect of the compounds may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Even the parenteral preparations may be made long-acting, by dissolving or suspending the compound in oily or emulsified vehicles which allow it to disperse only slowly in the serum.

The term "prodrug" means compounds that are transformed in vivo to yield a compound of the present invention. The transformation may occur by various mechanisms, such as through hydrolysis in blood. A good discussion of the use of prodrugs is provided by T. Higuchi and W. Stella, "Pro-drugs as Novel Delivery Systems," Vol. 14 of the *A.C.S. Symposium Series*, and in *Bioreversible Carriers in Drug Design*, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as ($C_1$–$C_8$) alkyl, ($C_2$–$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N- ($C_1$–$C_2$)alkylamino($C_2$–$C_3$)alkyl (such as β-dimethylaminoethyl), carbamoyl-($C_1$–$C_2$)alkyl, N,N-di ($C_1$–$C_2$)alkylcarbamoyl-($C_1$–$C_2$)alkyl and piperidino-, pyrrolidino- or morpholino($C_2$–$C_3$)alkyl.

Similarly, if a compound of the present invention comprises an alcohol functional group, a prodrug can be formed by the replacement of the hydrogen atom of the alcohol group with a group such as ($C_1$–$C_6$)alkanoyloxymethyl, 1-(($C_1$–$C_6$)alkanoyloxy)ethyl, 1-methyl-1-(($C_1$–$C_6$) alkanoyloxy)ethyl, ($C_1$–$C_6$)alkoxycarbonyloxymethyl, N-($C_1$–$C_6$)alkoxycarbonylaminomethyl, succinoyl, ($C_1$–$C_6$) alkanoyl, (x-amino($C_1$–$C_4$)alkanoyl, arylacyl and (x-aminoacyl, or (x-aminoacyl-α-aminoacyl, where each α-aminoacyl group is independently selected from the naturally occurring L-amino acids, $P(O)(OH)_2$, —$P(O)(O(C_1$–$C_6)alkyl)_2$ or glycosyl (the radical resulting from the removal of a hydroxyl group of the hemiacetal form of a carbohydrate).

If a compound of the present invention comprises an amine functional group, a prodrug can be formed by the replacement of a hydrogen atom in the amine group with a group such as $R^X$-carbonyl, $R^{X}O$-carbonyl, $NR^XR^{X_1}$-carbonyl where $R^X$ and $R^{X_1}$ are each independently (($C_1$–$C_{10}$)alkyl, ($C_3$–$C_7$)cycloalkyl, benzyl, or $R^X$-carbonyl is a natural α-aminoacyl or natural α-aminoacyl-natural α-aminoacyl, —C(OH)C(O)O$Y^X$ wherein ($Y^X$ is H, ($C_1$–$C_6$)alkyl or benzyl), —C(O$Y^{X0}$) $Y^{X1}$ wherein $Y^{X0}$ is ($C_1$–$C_4$) alkyl and $Y^{X1}$ is (($C_1$–$C_6$)alkyl, carboxy($C_1$–$C_6$)alkyl, amino($C_1$–$C_4$) alkyl or mono-N- or di-N,N-($C_1$–$C_6$)alkylaminoalkyl, —C($Y^{X2}$) $Y^{X3}$ wherein $Y^{X2}$ is H or methyl and $Y^{X3}$ is mono-N- or di-N,N-($C_1$–$C_6$)alkylamino, morpholino, piperidin-1-yl or pyrrolidin-1-yl.

As used herein, the term "effective amount" means an amount of compound of the methods of the present invention that is capable of treating the symptoms of the described pathological conditions. The specific dose of a compound administered according to this invention will, of course, be determined by the particular circumstances surrounding the case including, for example, the compound administered, the route of administration, the state of being of the subject, and the severity of the pathological condition being treated.

For the treatment of skin wrinkles, a preferred method of administration of the anti-wrinkle estrogen agonist/antagonist is by topical application. The topical pharmaceutical and cosmetic compositions of the present invention maybe made into a wide variety of product types. These include, but are not limited to lotions, creams, beach oils, gels, sticks, sprays, ointments, pastes, mousses and cosmetics. These product types may comprise several types of carrier systems including, but not limited to solutions, emulsions, gels and solids. The topical pharmaceutical and cosmetic compositions of the present invention formulated as solutions typically include a pharmaceutically-acceptable aqueous or organic solvent. The terms "pharmaceutically-acceptable aqueous solvent" and "pharmaceutically-acceptable organic solvent" refer to a solvent which is capable of having dissolved therein the anti-wrinkle estrogen agonist/antagonist, and possesses acceptable safety properties (e.g., irritation and sensitization characteristics). These solutions contain from about 0.00001% to about 20%, more preferably from about 0.001% to about 10% of the anti-wrinkle estrogen agonist/antagonist, and from about 80% to about 99.999%, more preferably from about 90% to about 99.9% of an acceptable aqueous or organic solvent. If the topical pharmaceutical and cosmetic compositions of the present invention are formulated as an aerosol and applied to the skin as a spray-on, a propellant is added to a solution composition. Examples of propellants useful herein include, but are not limited to, the chlorinated, fluorinated and chlorofluorinated lower molecular weight hydrocarbons. A more complete disclosure of propellants useful herein can be found in Sagarin, *Cosmetics Science and Technology*, 2nd Edition, Vol. 2, pp. 443–465 (1972). Topical pharmaceutical and cosmetic compositions of the present invention further comprise from about 2% to about 50% of a topical pharmaceutical and cosmetically-acceptable emollient. As used herein, "emollients" refer to materials used for the prevention or relief of dryness, as well as for the protection of the skin. A wide variety of suitable emollients are known and may be used herein. Sagarin, *Cosmetics, Science and Technology*, 2nd Edition, Vol. 1, pp. 32–43 (1972), contains numerous examples of suitable materials. Examples of classes of useful emollients include the following:

1. Hydrocarbon oils and waxes. Examples include mineral oil, petrolatum, paraffin, ceresin, ozokerite, microcrystalline wax, polyethylene, and perhydrosqualene.
2. Silicone oil, such as dimethyl polysiloxanes, methylphenyl polysiloxanes, water-soluble and alcohol-soluble silicone glycol copolymers.
3. Triglyceride esters, for example vegetable and animal fats and oils. Examples include castor oil, safflower oil, cotton seed oil, corn oil, olive oil, cod liver oil, almond oil, avocado oil, palm oil, sesame oil, and soybean oil.
4. Acetoglyceride esters, such as acetylated monoglycerides.
5. Ethoxylated glycerides, such as ethoxylated glycerylmonostearate.
6. Alkyl esters of fatty acids having 10 to 20 carbon atoms. Methyl, isopropyl, and butyl esters of fatty acids are particularly useful herein. Examples of other useful alkyl esters include hexyl laurate, isohexyl laurate, iso-hexyl palmitate, isopropyl palmitate, decyl oleate, isodecyl oleate, hexadecyl stearate, decyl stearate, isopropyl isostearate, diisopropyl adipate, dissohexyl adipate, di-hexyldecyl adipate, diisopropyl sebacate, lauryl lactate, myristyl lactate, and cetyl lactate.
7. Alkenyl esters of fatty acids having 10 to 20 carbon atoms. Examples include oleyl myristate, oleyl stearate, and oleyl oleate.
8. Fatty acids having 10 to 20 carbon atoms. Suitable examples include pelargonic, lauric, myristic, palmitic, stearic, isostearic, hydroxystearic, oleic, linoleic, ricinoleic, arachidic, behenic, and erucic acids.
9. Fatty alcohols having 10 to 20 carbon atoms. Lauryl, myristyl, cetyl, hexadecyl, stearyl, isostearyl, hydroxystearyl, oleyl, ricinoleyl, behenyl, and erucyl alcohols, as well as 2-octyl dodecanol, are examples of satisfactory fatty alcohols.
10. Fatty alcohol ethers. Ethoxylated fatty alcohols of 10 to 20 carbon atoms include the lauryl, cetyl, stearyl, isostearyl, oelyl, and cholesterol alcohols having attached thereto from 1 to 50 ethylene oxide groups or 1 to 50 propylene oxide groups.
11. Ether-esters such as fatty acid esters of ethoxylated fatty alcohols.
12. Lanolin and derivatives. Lanolin, lanolin oil, lanolin wax, lanolin alcohols, lanolin fatty acids, isopropyllanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysis of lanolin, ethoxylated hydrogenated lanolin, ethoxylated sorbitol lanolin, and liquid and semisolid lanolin absorption bases are illustrative of emollients derived from lanolin.
13. Polyhydric alcohols and polyether derivatives. Propylene glycol, dipropylene glycol, polypropylene glycols 2000 and 4000, polyoxyethylene polyoxypropylene glycols, polyoxypropylene polyoxyethylene glycols, glycerol, sorbitol, ethoxylated sorbitol, hydroxypropylsorbitol, polyethylene glycols 200–6000, methoxy polyethylene glycols 350, 550, 750, 2000 and 5000, poly[ethylene oxide] homopolymers (100,000–5,000,000), polyalkylene glycols and derivatives, hexylene glycol (2-methyl-2,4-pentanediol), 1,3-butylene glycol, 1,2,6-hexanetriol, ethohexadiol USP (2-ethyl,3-hexanediol), C15–C18 vicinal glycol, and polyoxypropylene derivatives of trimethylolpropane are examples of this case of materials.
14. Polydydric alcohol esters. Ethylene glycol mono-and di-fatty acid esters, diethylene glycol mono- and di-fatty acid esters, polyethylene glycol (200–6000) mono-and di-fatty acid esters, propylene glycol mono- and di-fatty acid esters, polypropylene glycol 2000 monooleate, polypropylene glycol 2000 monostearate, ethoxylatedpropylene glycol monostearate, glyceryl mono- and di-fatty acid esters, polyglycerol poly-fatty acid esters, ethoxylated glyceryl monostearate, 1,3-butylene glycolmonostearate, 1,3-butylene glycol distearate, polyoxyethylene polyol fatty acid ester, sorbitan fatty acid esters, and polyoxyethylene sorbitan fatty acid esters are satisfactory polyhydric alcohol esters for use herein.
15. Wax esters such as beeswax, spermaceti, myristyl myristate and stearyl stearate.
16. Beeswax derivatives, e.g., polyoxyethylene sorbitol beeswax. These are reaction products of beeswax with ethoxylated sorbitol of varying ethylene oxide content, forming a mixture of ether-esters.
17. Vegetable waxes including carnauba and candelilla waxes.
18. Phospholipids, such as lecithin and derivatives.
19. Sterols. Cholesterol and cholesterol fatty acid esters are examples thereof.
20. Amides such as fatty acid amides, ethoxylated fatty acid amides and solid fatty acid alkanolamides.

Particularly useful emollients which provide skin conditioning are glycerol, hexanetriol, butanetriol, lactic acid and its salts, urea, pyrrolidone carboxylic acid and its salts, amino acids, guanidine, diglycerol and triglycerol. A lotion can be made from a solution carrier system. Lotions typically comprise from about 0.00001% to about 20%, preferably from about 0.001% to about 10%, of the anti-wrinkle estrogen agonist/antagonist; from about 1% to about 20%, preferably from about 5% to about 10%, of an emollient; and from about 50% to about 90%, preferably from about 60% to about 80%, water. Another type of product that may be formulated from a solution carrier system is a cream. A cream of the present invention comprises from about 0.00001% to about 20%, preferably from about 0.001% to about 10%, of the anti-wrinkle estrogen agonist/antagonist; from about 5% to about 50%, preferably from about 10% to about 20%, of an emollient, and from about 45% to about 85%, preferably from about 50% to about 75%, water. Yet another type of product that may be formulated from a solution carrier system is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may also comprise from about 2% to about 10% of an emollient plus from about 0.1% to about 2% of a thickening agent. Examples of suitable thickening agents include: cellulose derivatives (e.g., methyl cellulose and hydroxy propylmethylcellulose), synthetic high molecular weight polymers (e.g., carboxyvinyl polymer and polyvinyl alcohol), plant hydrocolloids (e.g., karaya gum and tragacanth gum), clay thickeners (e.g., colloidal magnesium aluminum silicate and bentonite), and carboxyvinyl polymers(CARBOPOLS®; sold by B. F. Goodrich Company, such polymers are described in detail in U.S. Pat. No. 2,798,053, Brown, issued Jul. 2, 1975). A more complete disclosure of thickening agents useful herein can be found in Segarin, *Cosmetics, Science and Technology*, 2nd Edition, Vol. 1, pp.72–73 (1972). If the carrier is formulated as an emulsion, from about 1% to about 10%, preferably from about 2% to about 5%, of the carrier system comprises an emulsifier. Emulsifiers maybe nonionic, anionic or cationic. Suitable emulsifiers are disclosed in, for example, *McCutcheon's Detergents and Emulsifiers, North American Edition, pages* 317–324 (1986). Preferred emulsifiers are anionic or nonionic, although other types may also be used.

Lotions and creams can be formulated as emulsions as well as solutions. Typically such lotions comprise from about 0.00001% to about 20%, preferably from about 0.0001% to about 10%, of the anti-wrinkle estrogen agonist/antagonist; from about 1% to about 20%, preferably from about 5% to about 10%, of an emollient; from about 25% to about 75%, preferably from about 45% to about 95%, water; and from about 0.1% to about 10%, preferably from about 0.5% to about 5%, of an emulsifier. Such creams would typically comprise from about 0.00001% to about 20%, preferably from about 0.0001% to about 10%, of the anti-wrinkle estrogen agonist/antagonist; from about 1% to about 20%, preferably from about 5% to about 10%, of an emollient; from about 20% to about 80%, preferably from about 30% to about 70%, water; and from about 1% to about 10%, preferably from about 2% to about 5%, of an emulsifier.

Single emulsion skin care preparations, such as lotions and creams, of the oil-in-water type and water-in-oil type are well known in the cosmetic arts and are useful in the present invention. Multiphase emulsion compositions, such as the water-in-oil-in water type are also useful in the present invention. In general, such single or multiphase emulsions contain water, emollients and emulsifiers as essential ingredients. Triple emulsion carrier systems comprising an oil-in-water-in-silicone fluid emulsion composition are also useful in the present invention.

Another emulsion carrier system useful in the topical pharmaceutical and cosmetic compositions of the present invention is a microemulsion carrier system. Such a system preferably comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name Tweens) or other nonionics; and from about 7% to about 20% water. This carrier system is combined with from about 0.00001% to about 10% of the anti-wrinkle estrogen agonist/antagonist.

If the topical pharmaceutical and cosmetic compositions of the present invention are formulated as a gel or a cosmetic stick, a suitable amount of a thickening agent, as disclosed supra, is added to a cream or lotion formulation. The topical pharmaceutical and cosmetic compositions of the present invention may also be formulated as makeup products such as foundations. Foundations are solution or lotion-based with appropriate amounts of thickeners, pigments and fragrance. The topical pharmaceutical and cosmetic compositions of the present invention may contain, in addition to the aforementioned components, a wide variety of additional oil-soluble materials and/or water-soluble materials conventionally used in topical compositions, at their established levels. Various water-soluble materials may also be present in the compositions of this invention. These include humectants, such as glycerol, sorbitol, propylene glycol, alkoxylated glucose and hexanetriol, ethyl cellulose, polyvinylalcohol, carboxymethyl cellulose, vegetable gums and clays such as VEEGUM® (magnesium aluminum silicate, R. T. Vanderbilt, Inc.); proteins and poly peptides, preservatives such as the methyl, ethyl, propyl and butyl esters of hydroxybenzoic acid (Parabens®—Mallinckrodt Chemical Corporation), EDTA, methylisothiazolinone and imidazolidinyl ureas (Germall 115®—Sutton Laboratories); and an alkaline agent such as sodium hydroxide or potassium hydroxide to neutralize, if desired, part of the fatty acids or thickener which may be present. In addition, the topical compositions herein can contain conventional cosmetic adjuvants, such as dyes, opacifiers (e.g., titanium dioxide), pigments and perfumes. The topical pharmaceutical and cosmetic compositions of the present invention may also include a safe and effective amount of a penetration enhancing agent. A preferred amount of penetration enhancing agent is from about 1% to about 5% of the composition. Other conventional skin care product additives may also be included in the compositions of the present invention. For example, collagen, hyaluronic acid, elastin, hydrolysates, primrose oil, jojoba oil, epidermal growth factor, soybean saponins, mucopolysaccharides, and mixtures thereof may be used. Various vitamins may also be included in the compositions of the present invention. For example, Vitamin A, and derivatives thereof, Vitamin B2, biotin, pantothenic, Vitamin D, and mixtures thereof may be used.

The estrogen agonists/antagonists may also be incorporated into anti-wrinkle skin cleaning compositions. The skin cleaning compositions of the present invention comprise, in addition to the anti-wrinkle estrogen agonist/antagonist, a cosmetically acceptable surfactant. The term "cosmetically-acceptable surfactant" refers to a surfactant which is not only an effective skin cleanser, but also can be used without undue toxicity, irritation, allergic response, and the like. Furthermore, the surfactant must be capable of being commingled with the anti-wrinkle estrogen agonist/antagonist in a manner such that there is no interaction which would substantially reduce the efficacy of the composition for treating wrinkles in mammalian skin. The skin cleaning compositions of the present invention contain from about 0.00001% to about 20%, preferably from about 0.0001% to about 10%, of the anti-wrinkle estrogen agonist/antagonist and from about 1% to about 90%, preferably from about 5% to about 10%, of a cosmetically-acceptable surfactant. The physical form of the skin cleansing compositions is not critical. The compositions can be, for example, formulated as toilet bars, liquids, pastes, or mousses. Toilet bars are most preferred since this is the form of cleansing agent most commonly used to wash the skin. The surfactant component of the compositions of the present invention are selected from anionic, nonionic, zwitterionic, amphoteric and ampholytic surfactants, as well as mixtures of these surfactants. Such surfactants are well known to those skilled in the detergency art. The cleaning compositions of the present invention can optionally contain, at their art-established levels, materials which are conventionally used in skin cleansing compositions.

"Cosmetically-acceptable" vehicles and formulations refers to vehicles and formulations that can be used without undue toxicity, irritation, allergic response, and the like. Furthermore, the vehicle and formulation must be capable of being commingled with the anti-wrinkle estrogen agonist/antagonist in a manner such that there is no interaction which would substantially reduce the efficacy of the composition for treating wrinkles in mammalian skin.

Other skin care products for the treatment of skin wrinkles may contain combinations of active ingredients. Such combinations include:

A. Sunscreens and Sunblocks: Optimum regulation of skin wrinkling resulting from exposure to U.V. light can be obtained by using a combination of the anti-wrinkle estrogen agonist/antagonist of the present invention together with sunscreens or sunblocks. Useful sunblocks include, for example, zinc oxide and titanium dioxide. Photo damage is a predominant cause of skin wrinkling. Thus, for purposes of wrinkle prevention, the combination of the anti-wrinkle estrogen agonist/antagonist with a UVA and/or UVB sunscreen would be most desirable. The inclusion of sunscreens in compositions of the present invention will provide immediate protection against acute UV damage. Thus, the sunscreen will prevent further wrinkle formation caused by UV radiation, while the anti-wrinkle agent treats existing wrinkles and skin atrophy. A wide variety of conventional sunscreening agents are suitable for use in combination with the anti-wrinkle estrogen agonist/antagonist. Segarin, et al., at Chapter VII, pages 189 et seq., of *Cosmetics Science and Technology*, disclose numerous suitable agents. Specific suitable sunscreening agents include, for example: p-aminobenzoic acid, its salts and its derivatives (ethyl, iso-butyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropylene glycol esters); cinnamic acid derivatives (methyl and benzyl esters, α-phenyl cinnamonitrile; butyl cinnamoyl pyruvate); dihydroxycinnamic acid derivatives (umbelliferone, methyl umbelliferone, methylacetoumbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); dihydroxynaphthoic acid and its salts; o- and p-hydroxybiphenyidisulfonates; (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and itsderivatives (e.g., hexaethylether); (butyl carbotol)(6-propyl piperonyl) ether; hydroquinone; benzophenones (oxybenzone, sulisobenzone, dioxybenzone, benzoresorcinol, 2,2',4,4'tetrahydroxy-benzophenone, 2,2'-dihydroxy-4,4'-dimethoxybenzophenone, octabenzone; 4-isopropyidibenzoyl-methane; butylmethoxy dibenzoylmethane; etocrylene; and 4-isopropyldibenzoylmethane. Mixtures of sunscreen compounds may be used to optimize the desired sunscreen properties of the formulation. A safe and effective amount of sunscreen may be used in the compositions of the present invention. The sun-screening agent must be compatible with the anti-wrinkle agent estrogen agonist/antagonist. Generally the composition may comprise from about 1% to about 20%, preferably from about 2% to about 10%, of a sunscreening agent. Exact amounts will vary depending upon the sunscreen chosen and the desired Sun Protection Factor (SPF). An agent may also be added to any of the compositions of the present invention to improve the skin substantivity of those compositions, particularly to enhance their resistance to being washed off by water, or rubbed off.

B. Anti-inflammatory Agents: In a preferred wrinkle treating composition of the present invention, an anti-inflammatory agent is included as an active agent along with the anti-wrinkle estrogen agonist/antagonist. The inclusion of an anti-inflammatory agent enhances the wrinkle treating benefits of the compositions. The anti-inflammatory agent protects strongly in the UVA radiation range (though it also provides some UVB protection as well) thereby preventing further wrinkle formation caused by UV radiation, while the anti-wrinkle estrogen agonist/antagonist treats existing wrinkles. Thus the combination provides broad protection. The topical use of anti-inflammatory agents reduces photo-aging of the skin resulting from chronic exposure to UV radiation. A safe and effective amount of an anti-inflammatory agent may be added to the compositions of the present invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency. Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, conisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used.

A second class of anti-inflammatory agents which is useful in the compositions of the present invention includes the nonsteroidal anti-inflammatory agents. The variety of compounds encompassed by this group are well-known to those skilled in the art. For detailed disclosure of the chemical structure, synthesis, side effects, etc., of non-steroidal anti-inflammatory agents, reference may be made to standard texts, including *Anti-inflammatory and Anti-*

*Rheumatic Drugs*, K. D. Rainsford, Vol. I–III,CRC Press, Boca Raton, (1985), and *Anti-inflammatory Agents, Chemistry and Pharmacology,* 1, R. A. Scherrer, et al., Academic Press, New York (1974). Specific non-steroidal anti-inflammatory agents useful in the composition of the present invention include, but are not limited to: 1) the oxicams, such as piroxicam, isoxicam, tenoxicam, and sudoxicam; 2) the salicylates, such as aspirin, disalcid, benorylate, trilisate, safapryn, solprin, diflunisal, and fendosal; 3) the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac; 4) the fenamates, such as mefenamic, meclofenamic, flufenamic, niflumic, and tolfenamic acids; 5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and 6) the pyrazoles, such as phenylbutazone, oxyphenbutazone, feprazone, azapropazone, and trimethazone. Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred. Yet another class of anti-inflammatory agents which are useful in the present invention are those disclosed in U.S. Pat. No. 4,912,248, Mueller, issued Mar. 27, 1990. This patent discloses compounds and diastereomeric mixtures of specific 2-naphthyl-containing ester compounds, especially naproxen ester and naproxol ester compounds, having two or more chiral centers. For example, compounds selected from (S)-naproxen-(S)-2-butyl ester, (S)-naproxen-(R)-2-butylester, (S)-naproxol-(R)-2-methylbutyrate, (S)-naproxol-(S)-2-methyl butyrate, diastereomeric mixtures of (S)-naproxen-(S)-2-butyl ester and (S)-naproxen-(R)-2-butyl ester, and diasteromeric mixtures of (S)-naproxol-(R)-2-methyl butyrate and (S)-naproxol-(S)-2-methyl butyrate are useful in the present invention. Finally, so-called "natural" anti-inflammatory agents are useful in the present invention. For example, candelilla wax, alpha bisabolol, aloe vera, Manjistha (extracted from plants in the genus Rubia, particularly *Rubia cordifolia*), and Guggal (extracted from plants in the genus Commiphora, particularly *Commiphora mukul*), may be used. Another preferred composition of the present invention comprises the anti-wrinkle estrogen agonist/antagonist, a sunscreen, and an anti-inflammatory agent together for wrinkle treatment.

C. Anti-Oxidants/Radical Scavengers: In a preferred wrinkle treating composition of the present invention, an antioxidant/radical scavenger is included as an active agent along with the anti-wrinkle estrogen agonist/antagonist. The inclusion of an anti-oxidant/radical scavenger increases the wrinkle treating benefits of the composition. A safe and effective amount of an anti-oxidant/radical scavenger may be added to the compositions of the present invention, preferably from about 0.1% to about 10%, more preferably from about 1% to about 5%, of the composition. Antioxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2 carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N diethylhydroxylamine, amino-guanidine), sulfhydryl compounds (e.g., glutathione), and dihydroxy fumaric acid and its salts maybe used. In a preferred wrinkle treating composition of the present invention, compositions comprise one, any two, or all three of a sun-screening agent, anti-inflammatory agent, and/or an antioxidant/radical scavenging agent included as actives along with the anti-wrinkle estrogen agonist/antagonist. The inclusion of two or all three of these agents with the anti-wrinkle estrogen agonist/antagonist increases the wrinkle treating benefits of the composition.

D. Chelators: In a preferred wrinkle treating composition of the present invention, a chelating agent is included as an active agent along with the anti-wrinkle estrogen agonist/antagonist. As used herein, "chelating agent" means an active agent capable of removing a metal ion from a system by forming a complex so that the metal ion cannot readily participate in or catalyze chemical reactions. The inclusion of a chelating agent increases the wrinkle treatment benefits of the composition. A safe and effective amount of a chelating agent maybe added to the compositions of the present invention, preferably from about 0.1% to about 10%, more preferably from about 1% to about 5%, of the composition. Preferred chelators useful in compositions of the present invention are furildioxime and derivatives thereof, more preferably amphi-2-furildioxime. In a preferred wrinkle and atrophy treating composition of the present invention, compositions comprise one, any two, any three, or all four of a sunscreening agent, anti-inflammatory agent, anti-oxidant/radical scavenging agent, and/or chelating agent included as actives along with the anti-wrinkle estrogen agonist/antagonist. The inclusion of two, three, or all four of these agents with the anti-wrinkle estrogen agonists I antagonists increases the wrinkle treatment benefits of the composition.

E. Retinoids: In a preferred wrinkle and atrophy treating composition of the present invention, a retinoid, preferably retinoic acid, is included as an active agent along with the anti-wrinkle estrogen agonist/antagonist. The inclusion of a retinoid increases the wrinkle treating benefits of the composition. A safe and effective amount of a retinoid may be added to the compositions of the present invention, preferably from about 0.001% to about 2%, more preferably from about 0.01% to about 1% of the composition. As used herein, "retinoid" includes all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid.

F. N-acetyl-L-cysteine: In a preferred anti-wrinkle composition of the present invention, N-acetyl-L-cysteine (NAC), is included as an active agent along with the anti-wrinkle estrogen agonist/antagonist. The inclusion of NAC increases the wrinkle treating benefits of the composition. A safe and effective amount of NAC may be added to the compositions of the present invention, preferably from about 0.1% to about 50% of the composition. In a preferred anti-wrinkle composition of the present invention compositions comprise one, any two, any three, any four, any five, and/or all six of a sun-screening agent, an anti-inflammatory agent, an antioxidant/radical scavenging agent, a chelating agent, a retinoid, and/or NAC included as actives along with the anti-wrinkle estrogen agonist/antagonist. The inclusion of two, three, four, five or six of these agents with the anti-wrinkle estrogen agonist/antagonist increases the wrinkle treating benefits of the composition.

Methods for Treating Wrinkles in Mammalian Skin:

The present invention further relates to a method for treating wrinkles in mammalian skin. Such a method comprises treating the skin with an effective amount of the anti-wrinkle estrogen agonist/antagonist. The amount of anti-wrinkle estrogen agonist/antagonist and frequency of treatment will vary widely depending upon the level of wrinkling already in existence in the subject, the rate of further wrinkle formation, and the level of regulation desired. A preferred method of treating the skin is via cutaneous injection of a safe and effective amount of the anti-wrinkle estrogen agonist/antagonist to treat wrinkles in mammalian skin. The carrier for injectable administration of the anti-wrinkle agent would preferably comprise water or a saline solution. The amount of anti-wrinkle estrogen agonist/antagonist and the frequency of cutaneous injection can vary widely, depending on personal needs.

A more preferred method of treating the skin is via topical application of a safe and effective amount of the anti-wrinkle estrogen antagonists/antagonists to treat wrinkles in mammalian skin. The amount of anti-wrinkle estrogen agonist/antagonist and frequency of topical application to the skin can vary widely, depending upon personal needs, but it is suggested as an example that topical application range from about once per week to about 10 times daily, preferably from about twice per week to about 4 times daily, more preferably from about 3 times a week to about twice daily, most preferably about once per day. The composition for topical application will comprise from about 0.00001% to about 20%, preferably from about 0.0001% to about 10% of the estrogen agonist/antagonist. The period of topical application would preferably be over a period of from about one month to about ten years. A preferred method of the present invention for treating wrinkles in mammalian skin involves applying both a safe and effective amount of the anti-wrinkle estrogen agonist/antagonist and a safe and effective amount of one or more of a sunscreening agent, an antiinflammatory agent, an anti-oxidant/radical scavenging agent, a chelating agent, and/or a retinoid to the skin simultaneously. As used herein, "simultaneous application" or "simultaneously" means applying the agents to the skin at the same sites on the body at about the same time. Though this can be accomplished by applying the agents separately to the skin, preferably a composition comprising all the desired agents commingled is applied to the skin. The amount of sunscreening agent applied is generally from about 0.02 mg to about 1.0 mg per $cm^2$ skin. The amount of anti-inflammatory agent applied is generally from about 0.005 mg to about 0.5 mg, preferably from about 0.01 mg to about 0.1 mg per $cm^2$ skin. The amount of anti-oxidant/radical scavenging agent generally applied is from about 0.001 mg to about 1.0 mg, preferably from about 0.05 mg to about 0.5 mg per $cm^2$ skin. The amount of chelating agent generally applied is from about 0.001 mg to about 1.0 mg, preferably from about 0.01 mg to about 0.5 mg, more preferably from about 0.05 mg to about 0.1 mg per $cm^2$ skin. The amount of retinoid applied is generally from about 0.00001 mg to about 0.02 mg per $cm^2$ skin, preferably from about 0.001 mg to about 0.01 mg per $cm^2$ skin. The amount of anti-wrinkle estrogen agonist/antagonist applied is generally from about 0.00001 mg to about 2 mg per $cm^2$ skin per application, preferably from about 0.0001 mg to about 1 mg per $cm^2$ skin per application.

Advantageously, the present invention also provides kits for use by a consumer for treating conditions responsive to estrogen such as rheumatoid arthritis, colon cancer, tissue wounds, skin wrinkles and cataracts. The kits comprise a) a pharmaceutical composition comprising an estrogen agonist/antagonist and a pharmaceutically acceptable carrier, vehicle or diluent; and b) instructions describing a method of using the pharmaceutical composition for treating conditions responsive to estrogen and/or specifically treating rheumatoid arthritis, colon cancer, tissue wounds, skin wrinkles and cataracts. The instructions may also indicate that the kit is for treating conditions responsive to estrogen and/or specifically treating rheumatoid arthritis, colon cancer, tissue wounds, skin wrinkles and cataracts while substantially reducing the concomitant liability of adverse effects associated with estrogen administration.

A "kit" as used in the instant application includes a container for containing the pharmaceutical compositions and may also include divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It maybe desirable to provide a written memory aid, where the written memory aid is of the type containing information and/or instructions for the physician, pharmacist or subject, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday," . . . etc . . . "Second Week, Monday, Tuesday, . . . " etc. Other variations of memory aids will be readily apparent. A "daily dose" can be a single tablet or capsule or several tablets or capsules to be taken on a given day. When the kit contains separate compositions, a daily dose of one or more compositions of the kit can consist of one tablet or capsule while a daily dose of another one or more compositions of the kit can consist of several tablet or capsules.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Based on a reading of the present description and claims, certain modifications to the compositions and methods described herein will be apparent to one of ordinary skill in the art. The claims appended hereto are intended to encompass these modifications.

All references and patents cited herein are incorporated by reference.

EXAMPLES

Example 1
Estrogen Receptor Binding.
Estrogen and estrogen agonist/antagonist binding affinity was measured by the following protocol:
cDNA cloning of human Eroα:
The coding region of human ERox was cloned by RT-PCR from human breast cancer cell mRNA using Expand™ High Fidelity PCR System according to manufacturer's instructions (Boehringer-Mannheim, Indianapolis, Ind.). PCR products were cloned into pCR2.1 TA Cloning Kit (Invitrogen, Carlsbad, Calif.) and sequenced. Each receptor coding region was subcloned into the mammalian expression vector pcDNA3 ((Invitrogen, Carlsbad, Calif.).

Mammalian Cell Expression.
Receptor proteins were overexpressed in 293T cells. These cells, derived from HEK293 cells (ATCC, Manassas, Va.), have been engineered to stably express large T antigen and can therefore replicate plasmids containing a SV40 origin of replication to high copy numbers. 293T cells were transfected with either hERα-pcDNA3 or hERβ-pcDNA3 using lipofectamine as described by the manufacturer (Gibco/BRL, Bethesda, Md.). Cells were harvested in phosphate buffered saline (PBS) with 0.5 mM EDTA at 48 h post-transfection. Cell pellets were washed once with PBS/EDTA. Whole cell lysates were prepared by homogenization in TEG buffer (50 mM Tris pH 7.4, 1.5 mM EDTA, 50 mM NaCl, 10% glycerol, 5 mM DTT, 5 µg/ml aprotinin, 10 µg/ml leupeptin, 0.1 mg/ml Pefabloc) using a dounce homogenizor. Extracts were centrifuged at 100,000×g for 2 h at 4 C and supernatants were collected. Total protein concentrations were determined using BioRad reagent (BioRad, Hercules, Calif.).

Competition Binding Assay.
The ability of various compounds to inhibit [$^3$H]-estradiol binding was measured by a competition binding assay using dextran-coated charcoal as has been described (Leake R E, Habib F 1987 Steroid hormone receptors: assay and characterization. In: B. Green and R. E. Leake (eds). Steroid Hormones a Practical Approach. IRL Press Ltd, Oxford. 67–92.) 293T cell extracts expressing either hERα or hERβ were incubated in the presence of increasing concentrations of competitor and a fixed concentration of [$^3$H]-estradiol (141 µCi/mmol, New England Nuclear, Boston, Mass.) in 50 mM TrisHCl pH 7.4, 1.5 mM EDTA, 50 mM NaCl, 10% glycerol, 5 mM DTT, 0.5 mg/mL β-lactoglobulin in a final volume of 0.2 mL. All competitors were dissolved in dimethylsulfoxide. The final concentration of receptor was 50 pM with 0.5 nM [$^3$H]-estradiol. After 16 h at 4 C, dextran-coated charcoal (20 µL) was added. After 15 min at room temperature the charcoal was removed by centrifugation and the radioactive ligand present in the supernatant was measured by scintillation counting. All reagents were obtained from Sigma (St. Louis, Mo.) unless otherwise indicated.

The binding affinity of (−)-cis-6-phenyl-5-[4-(2-pyrrolidin-1-yl-ethoxy)-phenyl]-5,6,7,8-tetrahydro-naphthalene-2-ol (PPTN) and 17α-estradiol were measured using recombinant human estrogen receptor (ER). FIG. 1 shows the results of a binding experiment in which the binding of PPTN was found to be similar to that of 17β-estradiol.

Example 2
Inhibition of In Vitro Human Breast Tumor Cell Growth.
The in vitro antiproliferative effects of (−)-cis-6-phenyl-5-[4-(2-pyrrolidin-1-yl-ethoxy)-phenyl]-5,6,7,8-tetrahydro-naphthalene-2-ol (PPTN) were tested using two types of human breast cancer cell lines: first, MCF-7 cells, which contain ER as well as progesterone receptors (PgR), and second, MDA-MB-231 cells, which lack ER and PgR, and enable the determination of an effect that is independent of the ER mechanism. The effect of PPTN on the growth of these different cell lines was determined by incubation of the cells with various compound concentrations for 6 days.

The antiproliferative effects were then determined by direct cell counts. PPTN inhibited the growth of the ER-positive cell line MCF-7. The $IC_{50}$ for growth inhibition was approximately 3 to 5×10$^{-11}$ M. In MDA-MB-231, ER-negative cell lines, the compound did not inhibit cell proliferation. These results indicate that growth inhibition was ER-specific and not due to cytotoxicity since the compound had no measurable effect on the ER-negative cell line.

Example 3
Treatment of Autoimmune Disease.
Treatment of spontaneous autoimmune diseases of MRL/Mp-Ipr/Ipr mice by administration of the estrogen agonists/antagonists of the present invention.

Eight-week old female MRL/Mp-Ipr/Ipr mice (Clea Japan, Inc.) are used in this examination. An estrogen agonist/antagonist as described herein is suspended in carboxymethylcellulose to prepare a 0.5% suspension. This compound is orally administered to each mouse once a day for 13 weeks at a dose of from 0.01 to 50 µg/day.

The spleen and lymph nodes of the MRL/Mp-Ipr/Ipr mice are seriously swollen with age due to the presence of the lymphoproliferation gene (Ipr). The Ipr codes for the Fas antigen in each mouse. However, in the MRL/Mp-Ipr/Ipr mice, an abnormality of the genes disturbs the expression of the Fas antigen. As a result, autoreactive T-cells are not subjected to negative selection through the Fas antigen in the thymus and appear in the peripheral tissues to cause the swelling of the lymphoid organs and autoimmune symptoms. The presence of the autoreactive T-cells was confirmed also in the autoimmune diseases of human beings, such as rheumatoid arthritis.

A reduction in swelling of the spleen and lymph nodes in the MRL/Mp-Ipr/Ipr mouse indicates that the estrogen agonists/antagonists of the present invention are capable of inhibiting the appearance of the autoreactive T-cells.

Example 4
Nitric Oxide Formation by Cultured Endothelial Cells

NO-formation is assessed by determination of intracellular cyclic GMP in cultured endothelial cells, whereas release of NO from these cells is measured by the stimulatory effect of NO on the activity of soluble guanylyl cyclase (Luckhoff, et al, *Br J Pharmacol,* 95:189, (1988); Wiemer, et al, *Hypertension,* 18:558, (1991); Linz, et al, *J Mol Cell Cardiol,* 24:909, (1992)).

Bovine or porcine aorta is obtained and endothelial cells are isolated by digestion with dispase. The cells are seeded on 6- or 24-well plates and grown to confluence. Dulbecco's modified Eagle's/Ham's F-12 medium containing 20% fetal calf serum is supplemented with penicillin (10 U/ml), streptomycin (10 mg/ml), L-glutamate (1 mM/l), glutathione (5 mg/ml), and L(+)ascorbic acid (5 mg/ml).

Primary cultures of endothelial cells are used. After removal of the culture medium by aspiration, the monolayer is washed twice with 2 ml HEPES-Tyrode's solution (37° C.). Thereafter, the cells are preincubated for 15 min at 37° C. with 3-isobutyl-1-methyl-xanthine (IBMX), ($10^{-4}$ M). After this time, compounds or solvents are added. After predetermined periods, the incubation medium is quickly removed. The cells are then immediately extracted with 0.6 ml 6% trichloroacetic acid and scraped off with a rubber scraper. The cell suspension is sonicated for 10 sec before being centrifuged for 5 min at 4,000 g. The supernatants are extracted with four volumes of water saturated diethylether, and the samples frozen (−20° C.) until analysis. The protein contents of the samples are measured according to Lowry, et al (*J Biol Chem,* 193:265, (1951)). Cyclic GMP can be determined in the acetylated samples by various methods (Heath et al, Which Cyclic GMP Assay?, in Moncada, S., et al., (eds) *The Biology of Nitric Oxide: 2 Enzymology, Biochemistry and Immunology.* Portland Press, London, pp 98,1992), e.g., using a commercially available radio-immunoassay (New England Nuclear). Cyclic GMP content is expressed as picomoles GMP per milligram protein.

Release of NO from endothelial cells is assayed on the basis of the stimulatory effect of NO on the activity of soluble guanylyl cyclase (purified from bovine lung) (Gerzer, et al, *Eur J Biochem* 116:479, (1981)). The activity of the enzyme is determined in terms of the formation of cyclic [$^{32}$P]GMP from α-[$^{32}$P]GTP. Reactions are carried out in a reaction mixture containing 30 mM triethanolamine HCl (pH 7.4), 1 mM reduced glutathione, 4 mM $MgCl_2$, 1 mM cGMP and 0.1 mg/ml bovine g-globulin (total volume of 0.18 ml) at 37° C. in the presence of a-[$^{32}$P]GTP (0.03 mM; 0.2 mCi) and soluble guanylyl cyclase (4 mg). Ten ml samples are quickly transferred to the reaction mixture. Enzymatic formation of cGMP is allowed to proceed for 60 sec and then stopped by the addition of 450 ml zinc acetate (120 mM) and 500 ml sodium carbonate (120 mM). A complete inhibition of cGMP formation can be achieved by preincubation of the monolayers for 30 min with the stereospecific inhibitor of NO synthase, $N^G$-nitro-L-arginine.

Time-response curves and dose-response curves are obtained after addition of the estrogen agonists/antagonists of the present invention. Data are reported as mean values ±SEM of cGMP (pmol/mg protein) or guanylyl cyclase activity (nmol/mg/min).

Example 5
In Vivo Measurement of Elastic Properties of Human Skin.

The effects of the estrogen agonist/antagonists of the present invention are measured on subjects using a modified Schade's instrument (Kirk, E. and Koorning, S. A., J. Gerontol. 4,:273, (1969)) as described by Dikstein and Hartzshtark In Chapter 6, In vivo measurement of some elastic properties of human skin, in *Bioengineering and the Skin,* Marks, R. and Payne, P. A. eds., 1981, MTP Press Ltd., Lancaster, England.

The measuring area of the instrument is a piece of plastic material (made of Teflon®) having a surface area of 0.2 $cm^2$. It is connected to a light metal measuring rod counterbalanced so that the net pressure of the system is less than 1 $g/cm^2$. The measuring rod can be loaded with weights, thereby increasing the pressure to any desired value. The measuring rod is connected to a linear variable differential transformer (LVDT). The output of the LVDT is graphically recorded or electronically stored for later analysis. A standard area of facial skin (such as the center of the forehead) is selected for measurement.

The subject lays on his or her back with eyes closed. The measuring rod is adjusted to touch the skin and the baseline output of the LVDT transducer system recorded until stabilized. After the baseline is stabilized, a standard weight (sufficient to exert 10 $g/cm^2$ force) is applied. Indentation of the measuring rod is recorded for 10 seconds and then the weight is removed from the measuring rod and the rebound is recorded for an additional 10 seconds. The percentage rebound is calculated by dividing rebound distance by total indentation. Using a range of weights on the measuring rod to achieve a pressure range of 10 to 100 $g/cm^2$, a depth of indentation versus pressure curve is calculated for the test area of skin. The rebound and indentation versus pressure measurements are performed on the subject prior to dosing with an estrogen agonist/antagonist of the present invention. The subject is then dosed with estrogen agonist/antagonist or the subject is instructed to daily apply a topical composition comprising the estrogen agonist/antagonist of the present invention. Measurements of skin elasticity are repeated at 1, 3 and 6 months of dosing. An increase in skin elasticity associated with a reduction in wrinkles is indicated with an increased rebound score and steeper depth of penetration versus pressure relationship.

Example 6
Inhibition of Cataract Formation.

The effects of the estrogen agonists/antagonists of the present invention are assessed on female Sprague-Dawley rats. At an age of 45 to 60 days, rats are ovariectomized. Each animal receives a single intravenous injection of 50 mg/kg methyinitrosourea (MNU (dissolved in phosphate-buffered saline (PBS) and injected through the tail vein within 15 minutes of preparation) and a treatment Silasitic® capsule containing estrogen agonist/antagonist is placed subcutaneously on the back. A placebo group receives an empty Silastic® capsule. Non-ovariectomized rats are also injected with MNU and serve as the normal animal control.

The eyes of each animal are examined daily for gross changes and abnormalities. At 40 weeks post MNU injection, the animals are euthanized. Entire eyes are removed from the euthanized animals, slit open across the cornea and immersed in fixative (neutral formalin/ethanol/acetic acid/water 2:3:1:3) for 2 weeks as described by Roy et al., Hiroshima *J. Med. Sci.,* 38:95–98, (1989). The eyes are then processed and embedded in paraffin. Six-micrometer sections are prepared and stained with hematoxylin and eosin for examination of lens histology.

For the measurement of corneal opacity, the eyes of euthanized estrogen agonist/antagonist treated animals and euthanized ovariectomized placebo control animals are extruded and slit open around the cornea and the lenses carefully removed. The lens from each eye is placed in a shallow culture dish containing PBS. The dish is placed on the stage of dissecting microscope with its zoom objective lens set at 1.5×; a charge-coupled device color video camera (model DXC-960MD, Sony) is attached to one ocular. The lens is viewed with transmitted light and the image captured using an imaging program (IPLAB SPECTRUM, Signal Analytics, Vienna, Va.) run on a computer. A 2-mm thick piece (1 cm square) of opaque, white Teflon is included in the microscope field for measurement of transmitted light. The intensity of transmitted light (in arbitrary units) transmitted at the center of the lens is measured by the imaging program. Likewise, the intensity of light transmitted through the culture dish to a position outside the lens is measured to define 100% transmission. The units of light measured from the Teflon® piece are considered background and are used to correct the light transmission measurements made for the lens and outside the lens. The light passing through the lens is calculated as the percentage transmission.

What is claimed is:

1. A method of treating colon cancer, the method comprising administering to a subject in need thereof, an effective amount of (−)-cis-6-phenyl-5-[4-(2-pyrrolidin-1-yl-ethoxy)-phenyl]-5,6,7,8-tetrahydro-naphthalene-2-ol or an optical or geometric isomer thereof; or a nontoxic pharmacologically acceptable acid addition salt or ester thereof.

2. The method of claim 1 wherein the (−)-cis-6-phenyl-5-[4-(2-pyrrolidin-1-yl-ethoxy)-phenyl]-5,6,7,8-tetrahydro-naphthalene-2-ol is in the form of a nontoxic pharmacologically acceptable acid addition salt, and the salt is the D-tartrate.

* * * * *